(12) United States Patent
Mitsuhashi

(10) Patent No.: US 8,268,982 B2
(45) Date of Patent: Sep. 18, 2012

(54) PRIMERS AND PROBES FOR THE DETECTION OF HIV

(75) Inventor: Masato Mitsuhashi, Irvine, CA (US)

(73) Assignees: Hitachi Chemical Co., Ltd., Shinjuku-ku, Toyko (JP); Hitachi Chemical Research Center, Inc., Irvine, CA (US)

(*) Notice: Subject to any disclaimer, the term of this patent is extended or adjusted under 35 U.S.C. 154(b) by 947 days.

(21) Appl. No.: 10/585,393

(22) PCT Filed: Jan. 7, 2005

(86) PCT No.: PCT/US2005/000504
§ 371 (c)(1),
(2), (4) Date: Apr. 24, 2009

(87) PCT Pub. No.: WO2005/067646
PCT Pub. Date: Jul. 28, 2005

(65) Prior Publication Data
US 2009/0226886 A1   Sep. 10, 2009

Related U.S. Application Data

(60) Provisional application No. 60/534,754, filed on Jan. 7, 2004.

(51) Int. Cl.
*C07H 21/04* (2006.01)
*C12Q 1/68* (2006.01)
*C12P 19/34* (2006.01)
*C12N 9/00* (2006.01)

(52) U.S. Cl. .............. 536/24.3; 435/6.12; 435/91.2; 435/183

(58) Field of Classification Search .............. None
See application file for complete search history.

(56) References Cited

U.S. PATENT DOCUMENTS

| | | |
|---|---|---|
| 5,491,063 A | 2/1996 | Fisher et al. |
| 6,001,558 A | 12/1999 | Backus et al. |
| 6,391,544 B1 | 5/2002 | Salituro et al. |
| 6,589,734 B1 | 7/2003 | Kacian et al. |
| 2003/0148280 A1 | 8/2003 | Harris et al. |

FOREIGN PATENT DOCUMENTS

| | | |
|---|---|---|
| EP | 1 344 837 A1 | 9/2003 |
| WO | WO 91/08308 | 6/1991 |
| WO | WO 01/04361 A2 | 1/2001 |
| WO | WO 03/020878 A2 | 3/2003 |

OTHER PUBLICATIONS

Lowe et al. A computer program for selection of oligonucleotide primers for polymerase chain reactions. Nucleic Acids Res. (1990) vol. 18, No. 7, pp. 1757-1761.*
"Diagnosis of human immunodeficiency virus infection by a polymerase chain reaction assay evaluated in patients harbouring strains of diverse geographical origin"; Kristel Van Laethem, et al.; Journal of Virological Methods 70 (1998) 153-166.
International Search Report.
Written Opinion of the International Search Report.
"Quantification of Human Immunodeficiency Virus Type 1 Proviral Load by a TaqMan Real-Time PCR Assay"; Nathalie Desire, et al.; Journal of Clinical Microbiology, Apr. 2001, pp. 1303-1310; vol. 39, No. 4.
"Exo-Proofreading, a Versatile SNP Scoring Technology"; Patrick Cahill, et al.; Genome Research, pp. 925-931, (2006).

* cited by examiner

*Primary Examiner* — Kenneth R. Horlick
*Assistant Examiner* — David Thomas
(74) *Attorney, Agent, or Firm* — Knobbe Martens Olson & Bear, LLP

(57) ABSTRACT

Provided herein are primer/probe sets useful for detecting HIV (HIV-1) in a test sample. The primer/probe sets can be employed according to nucleic acid amplification procedures including PCR, real-time quantitative PCR, or RT-PCR. The primer/probe sets can also be provided in the form of a kit with other reagents for performing a nucleic acid amplification reaction.

10 Claims, 3 Drawing Sheets

FIG 1. TaqMan real time PCR using 18 template oligonucleotides.
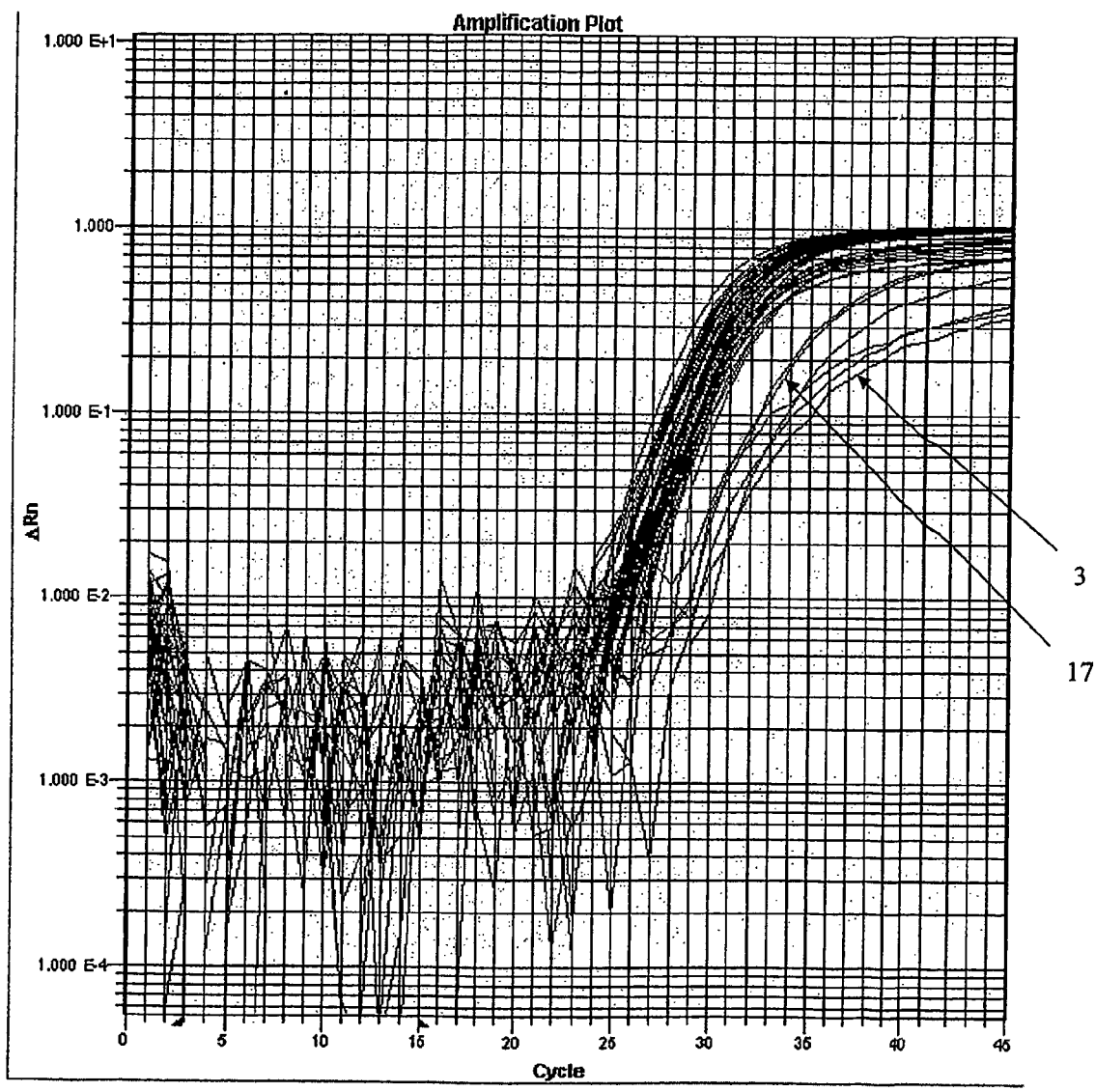

FIG 2. TaqMan real time PCR using 18 template oligonucleotides.
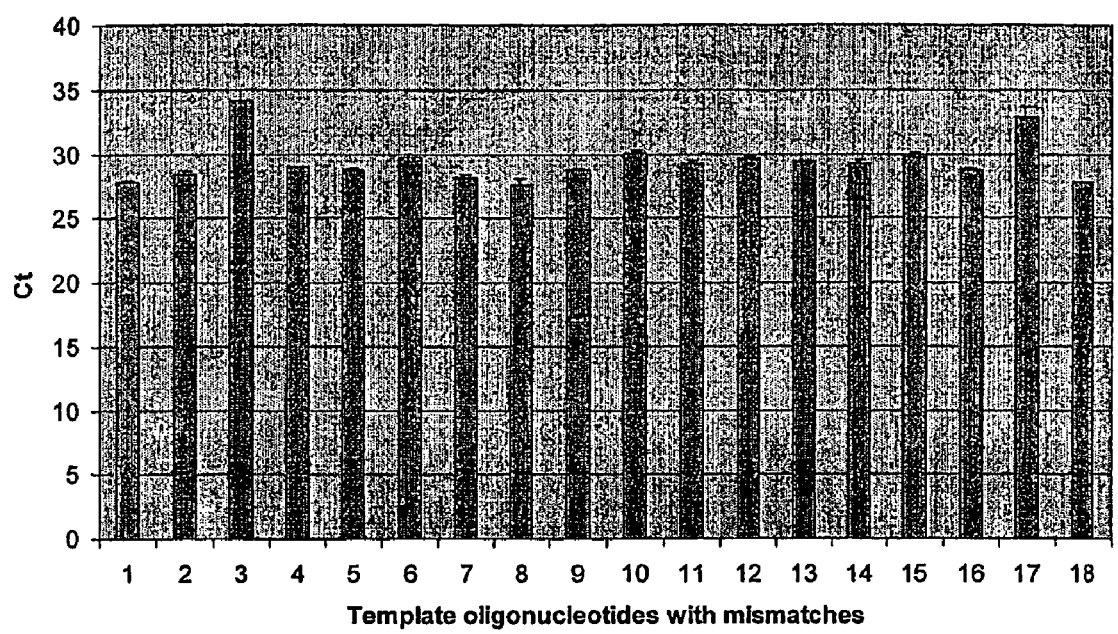

FIG 3. Amplification from HIV blood.
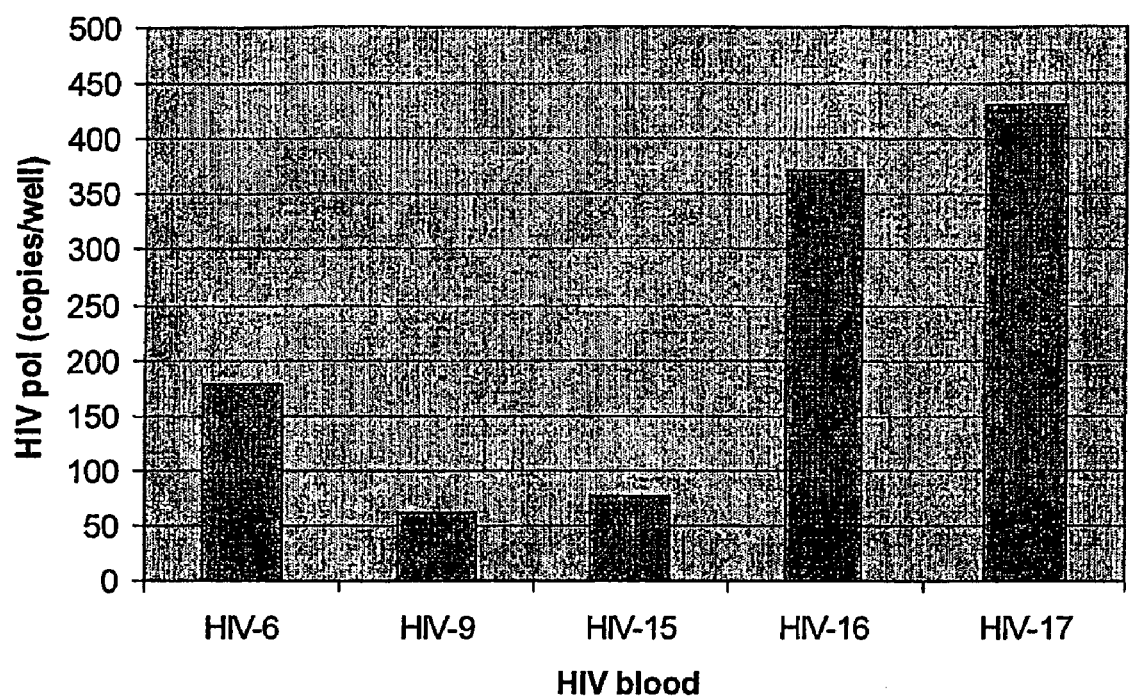

SEQUENCE LISTING

<160> NUMBER OF SEQ ID NOS: 27

<210> SEQ ID NO 1
<211> LENGTH: 28
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 3, 10, 24
<223> OTHER INFORMATION: n = A or G
<220> FEATURE:
<221> NAME/KEY: misc_feature
<222> LOCATION: 6
<223> OTHER INFORMATION: n = A, G, C, T, or U
<220> FEATURE:
<221> NAME/KEY: misc_feature
<222> LOCATION: 7, 9
<223> OTHER INFORMATION: n = C or T
<220> FEATURE:
<221> NAME/KEY: misc_feature
<222> LOCATION: 8
<223> OTHER INFORMATION: n = A, T, or U
<220> FEATURE:
<221> NAME/KEY: misc_feature
<222> LOCATION: 12
<223> OTHER INFORMATION: n = A, C, T, or U

<400> SEQUENCE: 1
gcngtnnnnn tncacaattt taanagaa                                           28

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide probe sequence
<220> FEATURE:
<221> NAME/KEY: misc_feature
<222> LOCATION: 17, 19, 22
<223> OTHER INFORMATION: n = G or C
<220> FEATURE:
<221> NAME/KEY: misc_feature
<222> LOCATION: 8, 11
<223> OTHER INFORMATION: n = A or G
<220> FEATURE:
<221> NAME/KEY: misc_feature
<222> LOCATION: 12, 21
<223> OTHER INFORMATION: n = A, G, T, or U
<220> FEATURE:
<221> NAME/KEY: misc_feature
<222> LOCATION: 15
<223> OTHER INFORMATION: n = C or T
<220> FEATURE:
<221> NAME/KEY: misc_feature
<222> LOCATION: 16, 18
<223> OTHER INFORMATION: n = A, T, or U

<400> SEQUENCE: 2
gggattgngg nntannnnc nng                                                 23

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 6, 18
<223> OTHER INFORMATION: n = C or T

```
<220> FEATURE:
<221> NAME/KEY: misc_feature
<222> LOCATION: 8
<223> OTHER INFORMATION: n = A, G, or C
<220> FEATURE:
<221> NAME/KEY: misc_feature
<222> LOCATION: 11
<223> OTHER INFORMATION: n = A, T, or U
<220> FEATURE:
<221> NAME/KEY: misc_feature
<222> LOCATION: 15, 17, 20
<223> OTHER INFORMATION: n = A or G

<400> SEQUENCE: 3
cgggtntntt ncagngnnan c                                        21

<210> SEQ ID NO 4
<211> LENGTH: 28
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 9, 12
<223> OTHER INFORMATION: n = C or T

<400> SEQUENCE: 4
gcagtattna tncacaattt taaaagaa                                 28

<210> SEQ ID NO 5
<211> LENGTH: 28
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 9, 12
<223> OTHER INFORMATION: n = C or T

<400> SEQUENCE: 5
gcagtgttna tncacaattt taaaagaa                                 28

<210> SEQ ID NO 6
<211> LENGTH: 28
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 9, 12
<223> OTHER INFORMATION: n = C or T

<400> SEQUENCE: 6
gcagtattna tncacaattt taagagaa                                 28

<210> SEQ ID NO 7
<211> LENGTH: 28
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 9
<223> OTHER INFORMATION: n = C or T

<400> SEQUENCE: 7
gcagtattna tacacaattt taaaagaa                                 28
```

```
<210> SEQ ID NO 8
<211> LENGTH: 28
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 9, 12
<223> OTHER INFORMATION: n = C or T

<400> SEQUENCE: 8
gcggttttna tncacaattt taaaagaa                                       28

<210> SEQ ID NO 9
<211> LENGTH: 28
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 9, 12
<223> OTHER INFORMATION: n = C or T

<400> SEQUENCE: 9
gcagtcttng tncacaattt taaaagaa                                       28

<210> SEQ ID NO 10
<211> LENGTH: 28
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 9, 12
<223> OTHER INFORMATION: n = C or T

<400> SEQUENCE: 10
gcagtattng tncacaattt taaaagaa                                       28

<210> SEQ ID NO 11
<211> LENGTH: 28
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 9, 12
<223> OTHER INFORMATION: n = C or T

<400> SEQUENCE: 11
gcagtgcana tncacaattt taaaagaa                                       28

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide probe sequence
<220> FEATURE:
<221> NAME/KEY: misc_feature
<222> LOCATION: 12
<223> OTHER INFORMATION: n = A or G
<220> FEATURE:
<221> NAME/KEY: misc_feature
<222> LOCATION: 17
<223> OTHER INFORMATION: n = G or C
```

```
-continued

<400> SEQUENCE: 12
gggattgggg gntacantgc agg                                           23

<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide probe  sequence
<220> FEATURE:
<221> NAME/KEY: misc_feature
<222> LOCATION: 17
<223> OTHER INFORMATION: n = G or C

<400> SEQUENCE: 13
gggattgggg attactntgc agg                                           23

<210> SEQ ID NO 14
<211> LENGTH: 23
<212> TYPE: DNA
<213> ORGANISM: Artificial Sequence
<220> FEATURE:
<223> OTHER INFORMATION: Synthetic oligonucleotide probe sequence
<220> FEATURE:
<221> NAME/KEY: misc_feature
<222> LOCATION: 12
<223> OTHER INFORMATION: n = A or G
<220> FEATURE:
<221> NAME/KEY: misc_feature
<222> LOCATION: 17
<223> OTHER INFORMATION: n = G or C

<400> SEQUENCE: 14
gggattgggg gntatantgc agg                                           23

<210> SEQ ID NO 15
<211> LENGTH: 23
<212> TYPE: DNA
<213> ORGANISM: Artificial Sequence
<220> FEATURE:
<223> OTHER INFORMATION: Synthetic oligonucleotide probe sequence
<220> FEATURE:
<221> NAME/KEY: misc_feature
<222> LOCATION: 12
<223> OTHER INFORMATION: n = A or G
<220> FEATURE:
<221> NAME/KEY: misc_feature
<222> LOCATION: 17
<223> OTHER INFORMATION: n = G or C

<400> SEQUENCE: 15
gggattgggg gntacantgc acg                                           23

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide probe sequence
<220> FEATURE:
<221> NAME/KEY: misc_feature
<222> LOCATION: 12
<223> OTHER INFORMATION: n = A or G
<220> FEATURE:
<221> NAME/KEY: misc_feature
<222> LOCATION: 17
<223> OTHER INFORMATION: n = G or C

<400> SEQUENCE: 16
gggattgggg gntacantgc ggg                                           23
```

```
<210> SEQ ID NO 17
<211> LENGTH: 23
<212> TYPE: DNA
<213> ORGANISM: Artificial Sequence
<220> FEATURE:
<223> OTHER INFORMATION: Synthetic oligonucleotide probe sequence
<220> FEATURE:
<221> NAME/KEY: misc_feature
<222> LOCATION: 12
<223> OTHER INFORMATION: n = A or G
<220> FEATURE:
<221> NAME/KEY: misc_feature
<222> LOCATION: 17
<223> OTHER INFORMATION: n = G or C

<400> SEQUENCE: 17
gggattgggg antacantgc agg                                              23

<210> SEQ ID NO 18
<211> LENGTH: 23
<212> TYPE: DNA
<213> ORGANISM: Artificial Sequence
<220> FEATURE:
<223> OTHER INFORMATION: Synthetic oligonucleotide probe sequence
<220> FEATURE:
<221> NAME/KEY: misc_feature
<222> LOCATION: 12
<223> OTHER INFORMATION: n = A or G
<220> FEATURE:
<221> NAME/KEY: misc_feature
<222> LOCATION: 17
<223> OTHER INFORMATION: n = G or C

<400> SEQUENCE: 18
gggattgagg gntacantgc agg                                              23

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 6
<223> OTHER INFORMATION: n = C or T
<220> FEATURE:
<221> NAME/KEY: misc_feature
<222> LOCATION: 15
<223> OTHER INFORMATION: n = A or G

<400> SEQUENCE: 19
cgggtntatt acagngacag c                                                21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 6
<223> OTHER INFORMATION: n = C or T
<220> FEATURE:
<221> NAME/KEY: misc_feature
<222> LOCATION: 15
<223> OTHER INFORMATION: n = A or G

<400> SEQUENCE: 20
cgggtntgtt acagngacag c                                                21
```

```
<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 6
<223> OTHER INFORMATION: n = C or T
<220> FEATURE:
<221> NAME/KEY: misc_feature
<222> LOCATION: 15
<223> OTHER INFORMATION: n = A or G

<400> SEQUENCE: 21
cgggtntatt acagngacaa c                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 6
<223> OTHER INFORMATION: n = C or T
<220> FEATURE:
<221> NAME/KEY: misc_feature
<222> LOCATION: 15
<223> OTHER INFORMATION: n = A or G

<400> SEQUENCE: 22
cgggtntatt acagnggcag c                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 6
<223> OTHER INFORMATION: n = C or T
<220> FEATURE:
<221> NAME/KEY: misc_feature
<222> LOCATION: 15
<223> OTHER INFORMATION: n = A or G

<400> SEQUENCE: 23
cgggtntatt tcagngacag c                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 6
<223> OTHER INFORMATION: n = C or T
<220> FEATURE:
<221> NAME/KEY: misc_feature
<222> LOCATION: 15
<223> OTHER INFORMATION: n = A or G

<400> SEQUENCE: 24
cgggtntatt acagngatag c                                              21
```

```
<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 6
<223> OTHER INFORMATION: n = C or T
<220> FEATURE:
<221> NAME/KEY: misc_feature
<222> LOCATION: 15
<223> OTHER INFORMATION: n = A or G

<400> SEQUENCE: 25
cgggtncatt acagngatag c                                              21

<210> SEQ ID NO 26
<211> LENGTH: 9719
<212> TYPE: DNA
<213> ORGANISM: Human immunodeficiency virus type 1
<220> FEATURE:
<223> OTHER INFORMATION: Synthetic oligonucleotide primer sequence

<400> SEQUENCE: 26
tggaagggct aattcactcc caacgaagac aagatatcct tgatctgtgg atctaccaca      60
cacaaggcta cttccctgat agcagaact  acacaccagg ccagggatc  agatatccac     120 tgacctttgg atggtgctac aagctagtac cagttgagcc agagaagtta agaagccca      180 acaaggaga gaacaccagc ttgttacacc ctgtgagcct gcatgaatg  gatgacccgg      240 agagagaagt gttagagtgg aggtttgaca gccgcctagc atttcatcac atggcccgag     300
agctgcatcc ggagtacttc aagaactgct gacatcgagc ttgctacaag gactttccg      360 ctggggactt tccagggagg cgtggcctgg gcgggactgg ggagtggcga gccctcagat     420
cctgcatata agcagctgct ttttgcctgt actgggtctc tctggttaga ccagatctga     480
gcctgggagc tctctggcta actagggaac ccactgctta agcctcaata aagcttgcct     540
tgagtgcttc aagtagtgtg tgcccgtctg ttgtgtgact ctggtaacta gagatccctc     600 agacccttttt agtcagtgtg gaaaatctct agcagtggcg cccgaacagg gacctgaaag     660
cgaaagggaa accagaggag ctctctcgac gcaggactcg gcttgctgaa gcgcgcacgg     720
caagaggcga ggggcggcga ctggtgagta cgccaaaaat tttgactagc ggaggctaga     780
aggagagaga tgggtgcgag agcgtcagta ttaagcgggg gagaattaga tcgatgggaa     840
aaaattcggt taaggccagg gggaaagaaa aatataaat  taaaacatat agtatgggca     900
agcagggagc tagaacgatt cgcagttaat cctggcctgt tagaaacatc agaaggctgt     960
agacaaatac tgggacagct acaaccatcc cttcagacag gatcagaaga acttagatca    1020
ttatataata cagtagcaac cctctattgt gtgcatcaaa ggatagagat aaaagacacc    1080
aaggaagctt tagacaagat agaggaagag caaaacaaaa gtaagaaaaa agcacagcaa    1140
gcagcagctg acacaggaca cagcaatcag gtcagccaaa attaccctat agtgcagaac    1200
atccaggggc aaatggtaca tcaggccata tcacctagaa ctttaaatgc atgggtaaaa    1260
gtagtagaag agaaggcttt cagcccagaa gtgatacccca tgttttcagc attatcagaa    1320
ggagccaccc cacaagattt aaacaccatg ctaaacacag tggggggaca tcaagcagcc    1380
atgcaaatgt taaaagagac catcaatgag gaagctgcag aatgggatag agtgcatcca    1440
gtgcatgcag ggcctattgc accaggccag atgagagaac caaggggaag tgacatagca    1500
ggaactacta gtaccctttca ggaacaaata ggatggatga caaataatcc acctatccca    1560
```

-continued

```
gtaggagaaa tttataaaag atggataatc ctgggattaa ataaaatagt aagaatgtat      1620
agccctacca gcattctgga cataagacaa ggaccaaagg aaccctttag agactatgta      1680
gaccggttct ataaaactct aagagccgag caagcttcac aggaggtaaa aaattggatg      1740
acagaaacct tgttggtcca aaatgcgaac ccagattgta agactatttt aaaagcattg      1800
ggaccagcgg ctacactaga agaaatgatg acagcatgtc agggagtagg aggacccggc      1860
cataaggcaa gagttttggc tgaagcaatg agccaagtaa caaattcagc taccataatg      1920
atgcagagag gcaattttag gaaccaaaga aagattgtta agtgtttcaa ttgtggcaaa      1980
gaagggcaca cagccagaaa ttgcagggcc cctaggaaaa agggctgttg gaaatgtgga      2040
aaggaaggac accaaatgaa agattgtact gagagacagg ctaattttt agggaagatc       2100 tggccttcct acaagggaag gccagggaat tttcttcaga gcagaccaga gccaacagcc      2160
ccaccagaag agagcttcag gtctggggta gagacaacaa ctccccctca gaagcaggag      2220
ccgatagaca aggaactgta tcctttaact tccctcaggt cactctttgg caacgacccc      2280
tcgtcacaat aaagataggg gggcaactaa aggaagctct attagataca ggagcagatg      2340
atacagtatt agaagaaatg agtttgccag gaagatggaa accaaaaatg ataggggggaa     2400 ttggaggttt tatcaaagta agacagtatg atcagatact catagaaatc tgtggacata      2460
aagctatagg tacagtatta gtaggaccta cacctgtcaa cataattgga agaaatctgt      2520
tgactcagat tggttgcact ttaaattttc ccattagccc tattgagact gtaccagtaa      2580
aattaaagcc aggaatggat ggcccaaaag ttaaacaatg gccattgaca gaagaaaaaa      2640
taaaagcatt agtagaaatt tgtacagaga tggaaaagga agggaaaatt tcaaaaattg      2700
ggcctgaaaa tccatacaat actccagtat ttgccataaa gaaaaaagac agtactaaat      2760
ggagaaaatt agtagatttc agagaactta ataagagaac tcaagacttc tgggaagttc      2820
aattaggaat accacatccc gcagggttaa aaagaaaaaa atcagtaaca gtactggatg      2880
tgggtgatgc atatttttca gttcccttag atgaagactt caggaagtat actgcattta      2940
ccatacctag tataaacaat gagacaccag ggattagata tcagtacaat gtgcttccac      3000
agggatggaa aggatcacca gcaatattcc aaagtagcat gacaaaaatc ttagagcctt      3060
ttagaaaaca aaatccagac atagttatct atcaatacat ggatgatttg tatgtaggat      3120
ctgacttaga aatagggcag catagaacaa aaatagagga gctgagacaa catctgttga      3180
ggtggggact taccacacca gacaaaaaac atcagaaaga acctccattc ctttggatgg      3240
gttatgaact ccatcctgat aaatggacag tacagcctat agtgctgcca gaaaaagaca      3300
gctggactgt caatgacata cagaagttag tggggaaatt gaattgggca agtcagattt      3360
acccagggat taaagtaagg caattatgta aactccttag aggaaccaaa gcactaacag      3420
aagtaatacc actaacagaa gaagcagagc tagaactggc agaaaacaga gagattctaa      3480
aagaaccagt acatggagtg tattatgacc catcaaaaga cttaatagca gaaatacaga      3540 agcagggca aggccaatgg acatatcaaa tttatcaaga gccatttaaa aatctgaaaa      3600
caggaaaata tgcaagaatg aggggtgccc acactaatga tgtaaaacaa ttaacagagg      3660
cagtgcaaaa aataaccaca gaaagcatag taatatgggg aaagactcct aaatttaaac      3720
tgcccataca aaaggaaaca tgggaaacat ggtggacaga gtattggcaa gccacctgga      3780
ttcctgagtg ggagtttgtt aatacccctc ccttagtgaa attatggtac cagttagaga      3840
aagaacccat agtaggagca gaaaccttct atgtagatgg ggcagctaac agggagacta      3900
aattaggaaa agcaggatat gttactaata gaggaagaca aaaagttgtc accctaactg      3960
```

```
acacaacaaa tcagaagact gagttacaag caatttatct agctttgcag gattcgggat    4020
tagaagtaaa catagtaaca gactcacaat atgcattagg aatcattcaa gcacaaccag    4080
atcaaagtga atcagagtta gtcaatcaaa taatagagca gttaataaaa aaggaaaagg    4140
tctatctggc atgggtacca gcacacaaag gaattggagg aaatgaacaa gtagataaat    4200
tagtcagtgc tggaatcagg aaagtactat ttttagatgg aatagataag gcccaagatg    4260
aacatgagaa atatcacagt aattggagag caatggctag tgattttaac ctgccacctg    4320
tagtagcaaa agaaatagta gccagctgtg ataaatgtca gctaaaagga gaagccatgc    4380
atggacaagt agactgtagt ccaggaatat ggcaactaga ttgtacacat ttagaaggaa    4440
aagttatcct ggtagcagtt catgtagcca gtggatatat agaagcagaa gttattccag    4500
cagaaacagg gcaggaaaca gcatattttc ttttaaaatt agcaggaaga tggccagtaa    4560
aaacaataca tactgacaat ggcagcaatt tcaccggtgc tacggttagg gccgcctgtt    4620
ggtgggcggg aatcaagcag gaatttggaa ttccctacaa tccccaaagt caaggagtag    4680
tagaatctat gaataaagaa ttaaagaaaa ttataggaca ggtaagagat caggctgaac    4740
atcttaagac agcagtacaa atggcagtat tcatccacaa ttttaaaaga aaaggggggga    4800 ttgggggta cagtgcaggg gaaagaatag tagacataat agcaacagac atacaaacta    4860
aagaattaca aaaacaaatt acaaaaattc aaaattttcg ggtttattac agggacagca    4920
gaaatccact ttggaaagga ccagcaaagc tcctctggaa aggtgaaggg gcagtagtaa    4980
tacaagataa tagtgacata aaagtagtgc caagaagaaa agcaaagatc attagggatt    5040
atggaaaaca gatggcaggt gatgattgtg tggcaagtag acaggatgag gattagaaca    5100
tggaaaagtt tagtaaaaca ccatatgtat gtttcaggga aagctagggg atggttttat    5160
agacatcact atgaaagccc tcatccaaga ataagttcag aagtacacat cccactaggg    5220
gatgctagat tggtaataac aacatattgg ggtctgcata caggagaaag agactggcat    5280
ttgggtcagg gagtctccat agaatggagg aaaaagagat atagcacaca agtagaccct    5340
gaactagcag accaactaat tcatctgtat tactttgact gtttttcaga ctctgctata    5400
agaaaggcct tattaggaca catagttagc cctaggtgtg aatatcaagc aggacataac    5460
aaggtaggat ctctacaata cttggcacta gcagcattaa taacaccaaa aaagataaag    5520
ccacctttgc ctagtgttac gaaactgaca gaggatagat ggaacaagcc ccagaagacc    5580
aagggccaca gagggagcca cacaatgaat ggacactaga gcttttagag gagcttaaga    5640
atgaagctgt tagacatttt cctaggattt ggctccatgg cttagggcaa catatctatg    5700
aaacttatgg ggatacttgg gcaggagtgg aagccataat aagaattctg caacaactgc    5760
tgtttatcca ttttcagaat tgggtgtcga catagcagaa taggcgttac tcgacagagg    5820
agagcaagaa atggagccag tagatcctag actagagccc tggaagcatc caggaagtca    5880
gcctaaaact gcttgtacca attgctattg taaaaagtgt tgctttcatt gccaagtttg    5940
tttcataaca aaagccttag gcatctccta tggcaggaag aagcggagac agcgacgaag    6000
agctcatcag aacagtcaga ctcatcaagc ttctctatca aagcagtaag tagtacatgt    6060
aacgcaacct ataccaatag tagcaatagt agcattagta gtagcaataa taatagcaat    6120
agttgtgtgg tccatagtaa tcatagaata taggaaaata ttaagacaaa gaaaaataga    6180
caggttaatt gatagactaa tagaaagagc agaagacagt ggcaatgaga gtgaaggaga    6240
aatatcagca cttgtggaga tggggtgga gatgggcac catgctcctt gggatgttga    6300
tgatctgtag tgctacagaa aaattgtggg tcacagtcta ttatggggta cctgtgtgga    6360
```

```
aggaagcaac caccactcta ttttgtgcat cagatgctaa agcatatgat acagaggtac    6420
ataatgtttg ggccacacat gcctgtgtac ccacagaccc caacccacaa gaagtagtat    6480
tggtaaatgt gacagaaaat tttaacatgt ggaaaatgga catggtagaa cagatgcatg    6540
aggatataat cagtttatgg gatcaaagcc taaagccatg tgtaaaatta accccactct    6600
gtgttagttt aaagtgcact gatttgaaga atgatactaa taccaatagt agtagcggga    6660
gaatgataat ggagaaagga gagataaaaa actgctcttt caatatcagc acaagcataa    6720
gaggtaaggt gcagaaagaa tatgcatttt tttataaact tgatataata ccaatagata    6780
atgatactac cagctataag ttgacaagtt gtaacacctc agtcattaca caggcctgtc    6840
caaaggtatc ctttgagcca attcccatac attattgtgc cccggctggt tttgcgattc    6900
taaaatgtaa taataagacg ttcaatggaa caggaccatg tacaaatgtc agcacagtac    6960
aatgtacaca tggaattagg ccagtagtat caactcaact gctgttaaat ggcagtctag    7020
cagaagaaga ggtagtaatt agatctgtca atttcacgga caatgctaaa accataatag    7080
tacagctgaa cacatctgta gaattaatt gtacaagacc caacaacaat acaagaaaaa    7140
gaatccgtat ccagagagga ccaggggagag catttgttac aataggaaaa ataggaaata    7200
tgagacaagc acattgtaac attagtagag caaaatggaa taacacttta aaacagatag    7260
ctagcaaatt aagagaacaa tttggaaata ataaaacaat aatctttaag caatcctcag    7320
gaggggaccc agaaattgta acgcacagtt ttaattgtgg aggggaatttt ttctactgta    7380 attcaacaca actgtttaat agtacttggt ttaatagtac ttggagtact gaagggtcaa    7440
ataacactga aggaagtgac acaatcaccc tcccatgcag aataaaacaa attataaaca    7500
tgtggcagaa agtaggaaaa gcaatgtatg cccctcccat cagtggacaa attagatgtt    7560
catcaaatat tacagggctg ctattaacaa gagatggtgg taatagcaac aatgagtccg    7620
agatcttcag acctggagga ggagatatga gggacaattg gagaagtgaa ttatataaat    7680
ataaagtagt aaaaattgaa ccattaggag tagcacccac caaggcaaag agaagagtgg    7740
tgcagagaga aaaaagagca gtgggaatag gagctttgtt ccttgggttc ttgggagcag    7800
caggaagcac tatgggcgca gcctcaatga cgctgacggt acaggccaga caattattgt    7860
ctggtatagt gcagcagcag aacaatttgc tgagggctat tgaggcgcaa cagcatctgt    7920
tgcaactcac agtctggggc atcaagcagc tccaggcaag aatcctggct gtggaaagat    7980
acctaaagga tcaacagctc ctggggattt ggggttgctc tggaaaactc atttgcacca    8040
ctgctgtgcc ttggaatgct agttggagta ataaatctct ggaacagatt tggaatcaca    8100
cgacctggat ggagtgggac agagaaatta caattacac aagcttaata cactccttaa    8160
ttgaagaatc gcaaaaccag caagaaaaga atgaacaaga attattggaa ttagataaat    8220
gggcaagttt gtggaattgg tttaacataa caaattggct gtggtatata aaattattca    8280
taatgatagt aggaggcttg gtaggtttaa gaatagtttt tgctgtactt tctatagtga    8340
atagagttag gcagggatat tcaccattat cgtttcagac ccacctccca accccgaggg    8400
gacccgacag gcccgaagga atagaagaag aaggtggaga gagagacaga gacagatcca    8460
ttcgattagt gaacggatcc ttggcactta tctgggacga tctgcggagc ctgtgcctct    8520
tcagctacca ccgcttgaga gacttactct tgattgtaac gaggattgtg aacttctgg    8580 gacgcagggg gtgggaagcc ctcaaatatt ggtggaatct cctacagtat tggagtcagg    8640
aactaaagaa tagtgctgtt agcttgctca atgccacagc catagcagta gctgaggga    8700 cagatagggt tatagaagta gtacaaggag cttgtagagc tattcgccac atacctagaa    8760
```

-continued

```
gaataagaca gggcttggaa aggattttgc tataagatgg gtggcaagtg gtcaaaaagt    8820
agtgtgattg gatggcctac tgtaagggaa agaatgagac gagctgagcc agcagcagat    8880
agggtgggag cagcatctcg agacctggaa aaacatggag caatcacaag tagcaataca    8940
gcagctacca atgctgcttg tgcctggcta gaagcacaag aggaggagga ggtgggtttt    9000
ccagtcacac ctcaggtacc tttaagacca atgacttaca aggcagctgt agatcttagc    9060 cacttttaa aagaaaaggg gggactggaa gggctaattc actcccaaag aagacaagat     9120
atccttgatc tgtggatcta ccacacacaa ggctacttcc ctgattagca gaactacaca    9180
ccagggccag gggtcagata tccactgacc tttggatggt gctacaagct agtaccagtt    9240
gagccagata agatagaaga ggccaataaa ggagagaaca ccagcttgtt acaccctgtg    9300
agcctgcatg ggatggatga cccggagaga gaagtgttag agtggaggtt tgacagccgc    9360
ctagcatttc atcacgtggc ccgagagctg catccggagt acttcaagaa ctgctgacat    9420
cgagcttgct acaagggact ttccgctggg gactttccag ggaggcgtgg cctgggcggg    9480
actggggagt ggcgagccct cagatcctgc atataagcag ctgcttttg cctgtactgg     9540 gtctctctgg ttagaccaga tctgagcctg ggagctctct ggctaactag ggaacccact    9600
gcttaagcct caataaagct tgccttgagt gcttcaagta gtgtgtgccc gtctgttgtg    9660
tgactctggt aactagagat ccctcagacc cttttagtca gtgtggaaaa tctctagca     9719
```

<210> SEQ ID NO 27
<211> LENGTH: 23
<212> TYPE: DNA
<213> ORGANISM: Artificial Sequence
<220> FEATURE:
<223> OTHER INFORMATION: Synthetic oligonucleotide probe sequence
<220> FEATURE:
<221> NAME/KEY: misc_feature
<222> LOCATION: 12
<223> OTHER INFORMATION: n = A or G
<220> FEATURE:
<221> NAME/KEY: misc_feature
<222> LOCATION: 17
<223> OTHER INFORMATION: n = G or C

<400> SEQUENCE: 27
gggattgggg gntacanacc tgg                                              23

PRIMERS AND PROBES FOR THE DETECTION OF HIV

This application is a national phase of International Application No. PCT/US2005/000504 filed on Jan. 7, 2005, which is a non-provisional of Provisional Application No. 60/534,754 filed Jan. 7, 2004.

BACKGROUND OF THE INVENTION

1. Field of the Invention

The present invention relates to HIV. In particular the invention relates to oligonucleotides and methods for detecting HIV-1.

2. Description of the Related Art

Viruses classified as HIV contain RNA as their genetic information and the infectivity of HIV depends upon the virus's ability to insert its genetic information into the DNA of a host. In order to insert its genetic information and therefore successfully infect a host, an HIV virus must convert its genetic material (RNA) into DNA so that the HIV genetic information is compatible with that of the host. Apparently, HIV is successful at converting its RNA into DNA, given the prevalence of AIDS. However, while the virus may successfully convert RNA into DNA, the conversion is seldom accurate. In other words, the DNA copy of the viral RNA is not always exact and the DNA copy can diverge from the viral RNA by several base pairs. Hence, while a host initially may be infected with a single virus particle, after several rounds of replication, the host may be infected with a genetically diverse population of viruses.

Within each of the viral classifications of HIV-1 are several groups or subtypes. Because of the high frequency of mutation, HIV-1 has three major genetic groups, O, N, and M. In the M group, subtypes A, B, C, D, E, F, and G exist. Within each group and subtype, many mutations are found in different locations. Since the majority of the U.S. cases are Group M, subtype B, common primers and probes are widely available for subtype B. However, this system is not applicable to other groups and subtypes, and different systems should be used in various parts of the world, depending on the specific epidemic frequency. This means that there is no universal HIV detection system available at this time. Moreover, even in the US, negative test results cannot exclude the possibility of non-subtype B HIV-1 infection. This is particularly critical for blood transfusion. It is worth mentioning that all of these divisions are based upon the genetic variance between the viruses and, according to taxonomic theory, many of these viruses are the progeny of a single virus. Subtypes of HIV-1 are broken down even further into numerous categories. Hence, the numerous HIV types and subtypes demonstrate the highly mutable nature of HIV and the genetic variability of the HIV genome.

The genetic variability of the virus can be attributed to the inefficiency with which the virus converts its RNA into DNA, as mentioned above. Another theory concerning the genetic variability of the virus is that hosts can be infected with multiple different populations of HIV (which as mentioned above, can arise out of an infection by a single virus) and through the course of replication and packaging of the viral genetic information, pieces of one viral genome can be recombined with pieces of another viral genome. Hence, upon packaging of the recombined genome, a genetically distinct virus is formed. Regardless of the manner by which the virus mutates, it is clear that viruses known as HIV have genomes that are highly mutable and are therefore constantly changing. This presents those searching for methods of detecting the virus based upon its genetic information with a constantly moving target.

Hence, developing reagents and methods for detecting HIV based upon its genetic information is a continuing challenge.

SUMMARY OF THE INVENTION

The present invention provides reagents useful for detecting HIV (specifically, the various subtypes of HIV-1) based upon the genetic information of these viruses. In particular, the reagents are in the form of primer and probe sets which can be employed according to nucleic acid amplification procedures to specifically and sensitively detect various subtypes of HIV-1. Preferably, the primer/probe sets herein provided comprise two primer sequences and one probe sequence and are employed according to a reverse transcriptase (RT) PCR format. Particularly preferred embodiments are employed according to a TaqMan PCR format.

The present invention comprises various embodiments of two common primers (HIV-common-F (forward) and HIV-common-R (reverse)) and one probe (HIV-common-Probe), which were identified in the region of pol in the HXB2 genome.

The method for detecting HIV will generally comprise the steps of (a) forming a reaction mixture comprising nucleic acid amplification reagents, at least one primer/probe set mentioned above, and a test sample containing an HIV target sequence; (b) subjecting the mixture to amplification conditions to generate at least one copy of a nucleic acid sequence complementary to the target sequence; (c) hybridizing the probe to the nucleic acid sequence complementary to the target sequence, so as to form a hybrid comprising the probe and the nucleic acid sequence complementary to the target sequence; and (d) detecting the hybrid as an indication of the presence of HIV in the test sample.

The preferred RT PCR format will comprise the same steps as mentioned above but the amplification reagents will comprise an enzyme having reverse transcriptase activity. In addition, according to any of the methods provided herein, step (b) can be repeated multiple times to increase the number of target sequence copies. It will be understood by those skilled in the art that step (b) can be repeated through thermal cycling the reaction mixture.

The particularly preferred TaqMan format will comprise the same steps as described above, but the primer/probe set will comprise a probe labeled with a reporter dye (e.g., FAM, 6-carboxyfluorescein) and a quencher dye (e.g., TAMA, 6-carboxy-tetramethyl-rhodamine), and the amplification reagents will comprise the TaqMan polymerase, a DNA polymerase having 5'→3' exonuclease activity. The probe is rendered incapable of extension, for example by the presence of a 3' phosphate group. As the TaqMan polymerase encounters the labeled probe hybridized to the single-stranded DNA, it cleaves the probe and removes the reporter dye from spatial proximity to the quencher dye. This eliminates the quenching of the emission spectra of the reporter dye and allows the fluorescent activity of the reporter dye to be measured. Probe cleavage and the resultant increase in fluorescence is proportional to the amount of PCR product formed. The changes in fluorescence can be plotted against the number of cycles to generate an amplification plot such as that shown in FIG. 1. The intersection between the amplification plot and the threshold (defined as 10 times the standard deviation of the background fluorescence activity as measured between cycle 3 and 15) is known as the cycle threshold (Ct).

Other real-time PCR formats may also be employed. One format employs an intercalating dye, such as SYBR Green. This dye provides a strong fluorescent signal on binding double-stranded DNA; this signal enables quantification of the amplified DNA. Although this format does not permit sequence-specific monitoring of amplification, it enables direct quantization of amplified DNA without any labeled probes (see, e.g., Ponchel et al. (2003) Real-time PCR based on SYBR-Green I fluorescence: An alternative to the TaqMan assay for a relative quantification of gene rearrangements, gene amplifications and micro gene deletions. BMC Biotechnology 3:18). Other such fluorescent dyes that may also be employed are SYBR Gold, YO-PRO dyes and Yo Yo dyes.

Another real-time PCR format that may be employed uses reporter probes that hybridize to amplicons to generate a fluorescent signal. The hybridization events either separate the reporter and quencher moieties on the probes or bring them into closer proximity. The probes themselves are not degraded and the reporter fluorescent signal itself is not accumulated in the reaction. The accumulation of products during PCR is monitored by an increase in reporter fluorescent signal when probes hybridize to amplicons. Formats in this category include molecular beacons (Sanjay, T and Russell, K (1996) Molecular Beacons: Probes that Fluoresce upon Hybridization. Nature Biotech. Vol. 14, March, pp 303-308), dual-hybe probes (Cardullo et al. (1988) Detection of nucleic acid hybridization by nonradiative fluorescence resonance energy transfer. PNAS USA 85:8790-8794), Sunrise or Amplifluor (Nazarenko, et al. (1997) A closed tube format for amplification and detection of DNA based on energy transfer. Nucleic Acid Res. 25:2516-2521), and Scorpion (Whitcombe et al. (1999) Detection of PCR products using self quenching probing amplicons and fluorescence. Nature Biotech. 17:804-807) real-time PCR assays.

Another real-time PCR format that may also be employed is the so-called "Policeman" system. In this system, the primer comprises a fluorescent moiety, such as FAM, and a quencher moiety which is capable of quenching fluorescence of the fluorescent moiety, such as TAMRA, which is covalently bound to at least one nucleotide base at the 3' end of the primer. At the 3' end, the primer has at least one mismatched base and thus does not complement the nucleic acid sample at that base or bases. The template nucleic acid sequence is amplified by PCR with a polymerase having 3'-5' exonuclease activity, such as the Pfu enzyme, to produce a PCR product. The mismatched base(s) bound to the quencher moiety are cleaved from the 3' end of the PCR product by 3'-5' exonuclease activity. The fluorescence that results when the mismatched base with the covalently bound quencher moiety is cleaved by the polymerase, thus removing the quenching effect on the fluorescent moiety, is detected and/or quantified at least one time point during PCR. Fluorescence above background indicates the presence of the synthesized nucleic acid sample. This PCR format is described in detail in U.S. patent application Ser. No. 10/309,691, which is incorporated here by reference.

BRIEF DESCRIPTION OF THE DRAWINGS

FIGS. 1-2 show TaqMan real time PCR using eighteen template oligonucleotides.

FIG. 3 shows amplification from HIV blood.

DETAILED DESCRIPTION OF THE PREFERRED EMBODIMENT

The primer/probe sets provided herein comprise two primers and at least one probe. These primer/probe sets can be employed according to nucleic acid amplification techniques. Hence, the primers in any particular primer/probe set can be employed to amplify a target sequence. In most cases, the probe hybridizes to the copies of the target sequence generated by one of the primers and generally facilitates detecting any copies of the target sequence generated during the course of the amplification reaction. All of the primer/probe sets can be employed according to nucleic acid amplification procedures to specifically and sensitively detect HIV-1 groups M, N, and 0, as well as the various subtypes of HIV-1. Primer/probe sets for detecting HIV-1 subtypes are presented below in Table 1. Oligonucleotides complementary to the sequences listed in Table 1 may also be preferably used in the present invention.

TABLE 1

Template oligonucleotide primers and probes.

| Seq ID # | Forward Primer | Seq ID # | Probe | Seq ID # | Reverse Primer |
|---|---|---|---|---|---|
| 1 | 5'-GCRGT NYWYR THCAC AATTT TAARA GAA-3' | 2 | 5'-GGGAT TGRGG RDTAY WSWSC DSG-3' | 3 | 5'-CGGGT YTVTT WCAGR GRYAR C-3' |

Key
Y: C or T
R: A or G
S: G or C
N: A, G, C, T or U
W: A, T or U
D: A, G, T or U
V: A, G or C
H: A, C, T or U

As alluded to above, primers included in Table 1 can be used to prime synthesis of copies of an HIV-1 target sequence in the case of SEQ ID NO:1 and 3. The remaining SEQ ID NO:2 can hybridize with the amplification products of either or both of the primer sequences found in Table 1. Hence, the probe sequences are also specific for the various subtypes of HIV-1. Preferred embodiments of the invention include oligonucleotides comprising at least 15 consecutive nucleotides from a sequence selected from the group consisting of SEQ ID NO:1, 2, and 3. Embodiments of the invention more preferably include oligonucleotides comprising at least 16 consecutive nucleotides from a sequence selected from the group consisting of SEQ ID NO:1, 2, and 3. Embodiments of the invention even more preferably include oligonucleotides comprising at least 17 consecutive nucleotides from a sequence selected from the group consisting of SEQ ID NO:1, 2, and 3. Embodiments of the invention even more preferably include oligonucleotides comprising at least 18 consecutive nucleotides from a sequence selected from the group consisting of SEQ ID NO:1, 2, and 3. Embodiments of the invention even more preferably include oligonucleotides comprising at least 19 consecutive nucleotides from a sequence selected from the group consisting of SEQ ID NO:1, 2, and 3. Embodiments of the invention even more preferably include oligonucleotides comprising at least 20 consecutive nucleotides from a sequence selected from the group consisting of SEQ ID NO:1, 2, and 3. Embodiments of the invention even more preferably include oligonucleotides comprising at least 21 consecutive nucleotides from a sequence selected from the group consisting of SEQ ID NO:1, 2, and 3.

Primer sequences generally comprise deoxyribonucleic acid (DNA), or ribonucleic acid (RNA). Probe sequences on the other hand may comprise DNA, RNA or nucleic acid analogs such as uncharged nucleic acid analogs including but not limited to peptide nucleic acids (PNAs) which are disclosed in International Patent Application WO 92/20702 or morpholino analogs which are described in U.S. Pat. Nos. 5,185,444; 5,034,506; and 5,142,047, all of which are herein incorporated by reference. Such sequences can routinely be synthesized using a variety of techniques currently available. For example, a sequence of DNA can be synthesized using conventional nucleotide phosphoramidite chemistry and the instruments available from Applied Biosystems, Inc, (Foster City, Calif.); DuPont (Wilmington, Del.); or Milligen (Bedford, Mass.). Similarly, and when desirable, the sequences can be labeled using methodologies well known in the art such as described in U.S. Pat. Nos. 5,464,746; 5,424,414; and 4,948,882, all of which are herein incorporated by reference.

The term "label" as used herein means a molecule or moiety having a property or characteristic which is capable of detection. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, light, and the like to enable detection of the label. When indirectly detectable labels are used, they are typically used in combination with a "conjugate". A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

The term "test sample" as used herein, means anything suspected of containing an HIV target sequence. The test sample is or can be derived from any biological source, such as for example, blood, ocular lens fluid, cerebral spinal fluid, milk, ascites fluid, synovial fluid, peritoneal fluid, amniotic fluid, tissue, fermentation broths, cell cultures and the like. The test sample can be used (i) directly as obtained from the source or (ii) following a pre-treatment to modify the character of the sample. Thus, the test sample can be pre-treated prior to use by, for example, preparing plasma from blood, disrupting cells or viral particles, preparing liquids from solid materials, diluting viscous fluids, filtering liquids, distilling liquids, concentrating liquids, inactivating interfering components, adding reagents, purifying nucleic acids, and the like.

A "target sequence" as used herein means a nucleic acid sequence that is detected, amplified, or both amplified and detected using the primer/probe sets herein provided. Additionally, while the term target sequence is sometimes referred to as single stranded, those skilled in the art will recognize that the target sequence may actually be double stranded. Thus, in cases where the target is double stranded, primer sequences of the present invention will amplify both strands of the target sequence.

As mentioned earlier, the primer sequences of any particular primer/probe set (by themselves or with additional oligonucleotides) can be used as amplification primers according to nucleic acid amplification procedures well known in the art. Such reactions include, but are not intended to be limited to, the polymerase chain reaction (PCR) described in U.S. Pat. Nos. 4,683,195 and 4,683,202, the ligase chain reaction (LCR) described in EP-A-320 308, and gap LCR (GLCR) described in U.S. Pat. No. 5,427,930, all of which are herein incorporated by reference. Generically, these exemplified amplification reactions generate multiple copies of a DNA target sequence.

In accordance with the present invention the target sequence may indeed be DNA, on the other hand in light of the RNA nature of the HIV genome, the primer/probe sets may be employed according to an "RT PCR" format which is described in U.S. Pat. Nos. 5,322,770 and 5,310,652, both of which are herein incorporated by reference. Briefly, the RT PCR format provides a method of transcribing a strand of DNA from an RNA target sequence. The copied DNA strand transcribed from the RNA target is commonly referred to as "cDNA" which then can serve as a template for amplification by any of the methods mentioned above. The process of generating cDNA shares many of the hybridization and extension principles surrounding other amplification methods such as PCR, but the enzyme employed should have reverse transcriptase activity. Enzymes having reverse transcriptase activity, as well as the RT PCR process, are well known to those of skill in the art. Additionally, other methods for synthesizing cDNA are also known and include U.S. Pat. No. 5,686,272, which is herein incorporated by reference.

According to a preferred embodiment, the primer/probe sets are employed in the "oligonucleotide hybridization PCR" (variably referred to herein as "OH PCR") amplification reaction. The reagents employed in the preferred method comprise at least one primer/probe set (designated herein as primer/probe sets 1-8), as well as other reagents for performing an amplification reaction. "Other reagents for performing an amplification reaction" or "nucleic acid amplification reagents" include reagents which are well known and may include, but are not limited to, an enzyme having polymerase activity; enzyme cofactors such as magnesium; salts; nicotinamide adenine dinucleotide (NAD); and deoxynucleotide triphosphates (dNTPs), such as for example deoxyadenine triphosphate, deoxyguanine triphosphate, deoxycytosine triphosphate and deoxythymine triphosphate.

One preferred method generally comprises the steps of (a) forming a reaction mixture comprising nucleic acid amplification reagents, at least one primer/probe set of the present invention, and a test sample suspected of containing a target sequence; (b) subjecting the mixture to amplification conditions to generate at least one copy of a nucleic acid sequence complementary to the target sequence; (c) hybridizing the probe to the nucleic acid sequence complementary to the target sequence, so as to form a hybrid comprising the probe and the nucleic acid sequence complementary to the target sequence; and (d) detecting the hybrid as an indication of the presence of the target sequence (HIV) in the sample. It will be understood that step (b) of the above method can be repeated several times prior to step (c) by thermal cycling the reaction mixture between 10 and 100 times, more typically between 20 and 60 times, as is well known in the art.

Amplification conditions are defined generally as conditions which promote annealing and extension of one or more nucleic acid sequences. It is well known in the art that such annealing is dependent in a rather predictable manner on several parameters, including temperature, ionic strength, sequence length, complementarity, and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures which are close to (i.e., within 10° C. of) the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

Once sequences are selected for a given diagnostic application, the G:C content and length will be known and can be accounted for in determining precisely what hybridization conditions will encompass. Since ionic strength is typically optimized for enzymatic activity, the only parameter left to vary is the temperature. Generally, the hybridization temperature is selected close to or at the Tm of the primers or probe. Thus, obtaining suitable hybridization conditions for a particular primer/probe set is well within ordinary skill of one practicing this art.

According to the OH PCR method, it is preferable to select primers, probes and reaction conditions such that the probe sequence has a lower melt temperature than the primer sequences so that upon placing the reaction mixture under amplification conditions copies of the target sequence or its complement (variably referred to as an amplicon) are produced at temperature above the Tm of the probe. After such copies are synthesized, they are denatured and the mixture is cooled to enable the formation of hybrids between the probes and any copies of the target or its complement. The rate of temperature reduction from the denaturation temperature down to a temperature at which the probes will bind to single stranded copies is preferably quite rapid, for example between about 8 minutes to about 15 minutes, and preferably less than 2 minutes. Such a rapid cooling favors hybrid formation between the copies of the target sequence and the probe rather than, for example, hybrid formation between complementary strands of the amplicon.

In cases where labels are employed to detect primer sequence products, primer sequences are labeled with either a capture label or a detection label. The probe sequence is used to hybridize with the sequence generated by the primer sequence, and typically hybridizes with a sequence that does not include the primer sequence. Similarly to the primer sequence, the probe sequence is also labeled with either a capture label or a detection label with the caveat that when the primer is labeled with a capture label the probe is labeled with a detection label and vice versa. Detection labels have the same definition as "labels" previously defined and "capture labels" are typically used to separate extension products, and probes associated with any such products, from other amplification reactants. Specific binding members (as previously defined) are well suited for this purpose. Also, probes used according to this method are preferably blocked at their 3' ends so that they are not extended under hybridization conditions. Methods for preventing extension of a probe are well known and are a matter of choice for one skilled in the art. Typically, adding a phosphate group to the 3' end of the probe will suffice for purposes of blocking extension of the probe.

Upon formation of the copy sequence/probe hybrids, the differential labels (i.e. capture and detection labels) on the copy sequence and probe sequence can be used to separate and detect such hybrids. Preferably, detection is performed according to the protocols used by the commercially available Abbott LCx® instrumentation (Abbott Laboratories; Abbott Park, Ill.).

As previously discussed, the target sequence may be DNA or the target sequence may be imbedded within the HIV genome and therefore the target sequence may be in the form of RNA. In cases where the target sequence is part of the HIV genome, it is preferable to include an enzyme having reverse transcriptase activity as part of the so-called nucleic acid amplification reagents to enable production of cDNA for subsequent amplification. According to this embodiment, the primer sequences also serve as primers for cDNA synthesis. Although the invention contemplates distinct steps of cDNA production and there amplification and detection of amplified cDNA sequences, it will be understood that these processes may take place simultaneously in a single amplification reaction mixture.

The cDNA product or products can be isolated and recovered by conventional methods. Preferably the cDNA product or products are amplified. Any method for amplification may be used, including, without limitation, polymerase chain reaction (PCR), ligase chain reaction, strand displacement amplification, transcript mediated amplification, and nucleic acid single base amplification. Preferably, PCR is used. Typically, a reaction mixture containing all of the necessary components for PCR (including HIV-specific amplification primers) is added directly to the reverse transcription reaction mixture. Amplification is then carried out using conditions specified by the primer pairs that are used.

Following amplification, the amplification products may be detected using any method known in the art, including, without limitation, gel electrophoresis in agarose or acrylamide; capture of the amplification products on a solid support followed by colorimetric detection; ECi detection; fluorescence, radioisotopic detection, and chemiluminescence. Reagents for such detection methods are commercially available from, e.g, Molecular Probes, Eugene, Oreg., and Ortho Clinical Diagnostics, Rochester, N.Y.

One particularly preferred embodiment of the present invention comprises conducting real-time quantitative PCR (TaqMan) with the oligonucleotides of the present invention. Holland, et al., PNAS 88:7276-7280 (1991) describe an assay known as a Taqman assay. The 5' to 3' exonuclease activity of Taq polymerase is employed in a polymerase chain reaction product detection system to generate a specific detectable signal concomitantly with amplification. An oligonucleotide probe, nonextendable at the 3' end, labeled at the 5' end, and designed to hybridize within the target sequence, is introduced into the polymerase chain reaction assay. Annealing of the probe to one of the polymerase chain reaction product strands during the course of amplification generates a substrate suitable for exonuclease activity. During amplification, the 5' to 3' exonuclease activity of Taq polymerase degrades the probe into smaller fragments that can be differentiated from undegraded probe. The assay is sensitive and specific and is a significant improvement over more cumbersome detection methods. A version of this assay is also described in Gelfand et al., in U.S. Pat. Nos. 5,210,015. 5,210,015 to Gelfand, et al., and Holland, et al., PNAS 88:7276-7280 (1991) are hereby incorporated by reference.

Further, U.S. Pat. No. 5,491,063 to Fisher, et al., provides a Taqman-type assay. The method of Fisher et al. provides a reaction that results in the cleavage of single-stranded oligonucleotide probes labeled with a light-emitting label wherein the reaction is carried out in the presence of a DNA binding compound that interacts with the label to modify the light emission of the label. Suitable labels include, for example, FAM, HEX, TET, and JOE; rhodamine and derivatives such as Texas Red, ROX, and TAMRA; Lucifer Yellow, and coumarin derivatives such as 7-Me$_2$-N-coumarin-4-acetate, 7-OH-4-CH$_3$-coumarin-3-acetate, and 7-NH$_2$-4-CH$_3$-coumarin-3-acetate (AMCA). Suitable DNA binding compounds include, for example, ethidium bromide, acridine orange, proravine, acriflavine, fluorcoumarin, ellipticine, daunomycin, chloroquine, distamycin D, chromomycin, homidium, mithramycin, ruthenium polypyridyls, anthramycin, and so-called "groove binders" such as malachite green. The method utilizes the change in light emission of the labeled probe that results from degradation of the probe. The methods are applicable in general to assays that utilize a reaction that results in cleavage of oligonucleotide probes, and in particular, to homogeneous amplification/detection assays where hybridized probe is cleaved concomitant with primer extension. A homogeneous amplification/detection assay is provided which allows the simultaneous detection of the accumulation of amplified target and the sequence-specific detection of the target sequence. U.S. Pat. No. 5,491,063 to Fisher, et al. is hereby incorporated by reference.

The TaqMan detection assays offer several advantages over the classical PCR assays. First, the TaqMan assays combine the sensitivity of PCR along with hybridization of the internal oligonucleotide sequence that is present in an HIV sequence. Following PCR, samples do not have to be separated on agarose gels, and the subsequent Southern blots and hybridization steps that are necessary to verify the identity of the PCR products is eliminated. These additional post-PCR confirmation steps can easily add several days for an accurate identification. Using the TaqMan system, the assays are completed within 2.5 hours. Further, the methodology involved in the assay process makes possible the handling of large numbers of samples efficiently and without cross-contamination and is therefore adaptable for robotic sampling. As a result, large numbers of test samples can be processed in a very short period of time using the TaqMan assay. Another advantage of the TaqMan system is the potential for multiplexing. Since different fluorescent reporter dyes can be used to construct probes, several different HIV systems could be combined in the same PCR reaction, thereby reducing the labor costs that would be incurred if each of the tests were performed individually. The advantages of rapid, conclusive data together with labor and cost efficiency make the TaqMan detection system utilizing the specific primers of the invention a highly beneficial system for monitoring the presence of HIV.

The oligonucleotides of the present invention also can be provided as part of a kit useful for detecting HIV-1. The kits comprise one or more suitable containers containing one or more primer/probe sets according to the present invention, an enzyme having polymerase activity, deoxynucleotide triphosphates and, optionally, an enzyme having reverse transcriptase activity. Typically, at least one sequence bears a label, but detection is possible without this.

The following examples are provided to further illustrate the present invention and not intended to limit the invention.

EXAMPLE 1

In the present study, 2 common primers (HIV-common-F (forward) and HIV-common-R (reverse)) and 1 probe (HIV-common-Probe) were identified (Table 2, below), in the region of pol in the HXB2 genome (Table 3, below).

Four hundred µL of frozen heparinized blood from 5 HIV patients were thawed and applied to Leukosorb membrane-attached filterplates. Sixty µL of lysis buffer was then applied to the membrane, which was incubated at 37° C. for 1 hour. The filterplate was then placed on top of a GenePlate, and centrifuged at 300 rpm for five minutes to transfer the lysate to the GenePlate. The GenePlate was then incubated at 4° C. overnight. After washing the GenePlate with lysis buffer three times, followed by three applications of wash buffer, cDNA was synthesized in the wells of the GenePlate. The resultant cDNA was used for TaqMan assay using the common primers and probes as described above.

The resulting data was analyzed using two hundred sixty complete genome sequences of both HIV-1 and SIVcpz, viral sequence databases (GBVRL) downloaded from the GenBank, BLAST, PrimerAligner, PrimerExpress, and HYB-simulator.

TABLE II

Common primers and probes

HIV-common-F
(F-in-4794-28)

| QUERY | SEQ ID NO | | | |
|---|---|---|---|---|
| | 4 | GCAGTATTYA | TYCACAATTT | TAAAAGAA |
| A_SE.SE8131 | 4 | ---------- | ---------- | -------- |
| A_SE.UGSE8891 | 4 | ---------- | ---------- | -------- |
| A_SE.TZSE8538 | 4 | ---------- | ---------- | -------- |
| A_SE.UGSE6594 | 4 | ---------- | ---------- | -------- |
| A_KE.Q2317 | 4 | ---------- | ---------- | -------- |
| A_SE.UGSE7535 | 4 | ---------- | ---------- | -------- |
| A_SE.SOSE7253 | 4 | ---------- | ---------- | -------- |
| A_UG.92UG037 | 5 | -----G---- | ---------- | -------- |
| A_UG.U455 | 4 | ---------- | ---------- | -------- |
| B_US.DH123 | 4 | ---------- | ---------- | -------- |
| B_US.896 | 4 | ---------- | ---------- | -------- |
| B_US.MN | 4 | ---------- | ---------- | -------- |

TABLE II-continued

Common primers and probes

| | | |
|---|---|---|
| B_US.JRCSF | 4 | ---------- ---------- -------- |
| B_US.JRFL | 4 | ---------- ---------- -------- |
| B_US.YU10 | 4 | ---------- ---------- -------- |
| B_US.YU2 | 4 | ---------- ---------- -------- |
| B_AU.MBC200 | 4 | ---------- ---------- -------- |
| B_AU.MBC925 | 4 | ---------- ---------- -------- |
| B_US.BCSG3 | 4 | ---------- ---------- -------- |
| B_GA.OYI | 4 | ---------- ---------- -------- |
| B_GB.CAM1 | 4 | ---------- ---------- -------- |
| B_US.NY5CG | 4 | ---------- ---------- -------- |
| B_XX.NL43 | 4 | ---------- ---------- -------- |
| B_FR.LAI | 4 | ---------- ---------- -------- |
| B_FR.HXB2R | 4 | ---------- ---------- -------- |
| B_NL.ACH320A | 4 | ---------- ---------- -------- |
| B_NL.ACH320B | 4 | ---------- ---------- -------- |
| B_US.SF2CG | 4 | ---------- ---------- -------- |
| B_US.AD8 | 4 | ---------- ---------- -------- |
| B_DE.D31 | 4 | ---------- ---------- -------- |
| B_GB.MANC | 6 | ---------- ---------- ---G---- |
| B_DE.HAN2 | 4 | ---------- ---------- -------- |
| B_US.WEAU160 | 4 | ---------- ---------- -------- |
| B_US.RF | 4 | ---------- ---------- -------- |
| B_CN.RL42 | 4 | ---------- ---------- -------- |
| B_US.WR27 | 4 | ---------- ---------- -------- |
| C_BW.96BWO502 | 4 | ---------- ---------- -------- |
| C_IN.11246 | 4 | ---------- ---------- -------- |
| C_IN.301904 | 4 | ---------- ---------- -------- |
| C_IN.301905 | 4 | ---------- ---------- -------- |
| C_IN.21068 | 4 | ---------- ---------- -------- |
| C_IN.301999 | 4 | ---------- ---------- -------- |
| C_BR.92BR025 | 4 | ---------- ---------- -------- |
| C_ET.ETH2220 | 4 | ---------- ---------- -------- |
| D_ZR.Z2Z6 | 4 | ---------- ---------- -------- |
| D_ZR.ELI | 4 | ---------- ---------- -------- |
| D_ZR.NDK | 4 | ---------- ---------- -------- |
| D_ZR.84ZR085 | 6 | ---------- ---------- ---G---- |
| D_UG.94UG114 | 4 | ---------- ---------- -------- |
| F_VI850 | 4 | ---------- ---------- -------- |
| F_FI.FIN9363 | 4 | ---------- ---------- -------- |
| F_BR.93BR020 | 4 | ---------- ---------- -------- |
| G_FI.HH8793-11 | 4 | ---------- ---------- -------- |
| G_SE.SE6165 | 4 | ---------- ---------- -------- |
| G_BE.DRCBL | 4 | ---------- ---------- -------- |
| H_BE.VI991 | 4 | ---------- ---------- -------- |
| H_BE.VI997 | 4 | ---------- ---------- -------- |
| H_CF.90CF056 | 4 | ---------- ---------- -------- |
| J_SE.SE92809 | 7 | ---------- -A-------- -------- |
| J_SE.SE91733 | 7 | ---------- -A-------- -------- |
| AB_RU.KAL153-2 | 4 | ---------- ---------- -------- |
| AC_ZM.ZAM184 | 4 | ---------- ---------- -------- |
| AC_RW.92RW009 | 4 | ---------- ---------- -------- |
| AC_IN.21301 | 4 | ---------- ---------- -------- |
| ADI_ZR.MAL | 5 | -----G---- ---------- -------- |
| AE_CF.90CF402 | 4 | ---------- ---------- -------- |
| AE_TH.CM240 | 4 | ---------- ---------- -------- |
| AE_TH.93TH253 | 4 | ---------- ---------- -------- |
| AG_NG.IBNG | 4 | ---------- ---------- -------- |
| AG_DJ.DJ264 | 4 | ---------- ---------- -------- |
| AG_DJ.DJ263 | 4 | ---------- ---------- -------- |
| AG_NG.92NG003 | 4 | ---------- ---------- -------- |
| AG_NG.92NG083 | 4 | ---------- ---------- -------- |
| AGI_ZR.Z321B | 4 | ---------- ---------- -------- |
| AGI_CY.94CY0323 | 4 | ---------- ---------- -------- |
| AGI_GR.97PVCH | 4 | ---------- ---------- -------- |
| AGI_GR.97PVMY | 4 | ---------- ---------- -------- |
| AGJ_AU.BFP90 | 4 | ---------- ---------- -------- |
| BF_BR.93BR029 | 4 | ---------- ---------- -------- |
| N_CM.YBF30 | 8 | --G--T---- ---------- -------- |
| O_CM.MVP5180 | 9 | -----C---G ---------- -------- |
| O_CM.ANT70 | 10 | -------G-- ---------- -------- |
| SIVcpzUS | 4 | ---------- ---------- -------- |
| SIVCPZANT | 11 | -----GCA-- ---------- -------- |
| SIVCPZGAB | 5 | -----G---- ---------- -------- |

TABLE II-continued

Common primers and probes

HIV-common Probe
(P-1-4827-23)

| QUERY | SEQ ID NO | GGGATTGGGG GRTACASTGC AGG |
|---|---|---|
| A_SE.SE8131 | 12 | ---------- ---------- --- |
| A_SE.UGSE8891 | 12 | ---------- ---------- --- |
| A_SE.TZSE8538 | 12 | ---------- ---------- --- |
| A_SE.UGSE6594 | 12 | ---------- ---------- --- |
| A_KE.Q2317 | 12 | ---------- ---------- --- |
| A_SE.UGSE7535 | 12 | ---------- ---------- --- |
| A_SE.SOSE7253 | 12 | ---------- ---------- --- |
| A_UG.92UG037 | 12 | ---------- ---------- --- |
| A_UG.U455 | 12 | ---------- ---------- --- |
| B_US.DH123 | 12 | ---------- ---------- --- |
| B_US.896 | 12 | ---------- ---------- --- |
| B_US.MN | 12 | ---------- ---------- --- |
| B_US.JRCSF | 12 | ---------- ---------- --- |
| B_US.JRFL | 12 | ---------- ---------- --- |
| B_US.YU10 | 12 | ---------- ---------- --- |
| B_US.YU2 | 12 | ---------- ---------- --- |
| B_AU.MBC200 | 13 | ---------- AT---T---- --- |
| B_AU.MBC925 | 12 | ---------- ---------- --- |
| B_US.BCSG3 | 12 | ---------- ---------- --- |
| B_GA.OYI | 12 | ---------- ---------- --- |
| B_GB.CAM1 | 12 | ---------- ---------- --- |
| B_US.NY5CG | 12 | ---------- ---------- --- |
| B_XX.NL43 | 12 | ---------- ---------- --- |
| B_FR.LAI | 12 | ---------- ---------- --- |
| B_FR.HXB2R | 12 | ---------- ---------- --- |
| B_NL.ACH320A | 12 | ---------- ---------- --- |
| B_NL.ACH320B | 12 | ---------- ---------- --- |
| B_US.SF2CG | 12 | ---------- ---------- --- |
| B_US.AD8 | 12 | ---------- ---------- --- |
| B_DE.D31 | 12 | ---------- ---------- --- |
| B_GB.MANC | 12 | ---------- ---------- --- |
| B_DE.HAN2 | 12 | ---------- ---------- --- |
| B_US.WEAU160 | 12 | ---------- ---------- --- |
| B_US.RF | 12 | ---------- ---------- --- |
| B_CN.RL42 | 12 | ---------- ---------- --- |
| B_US.WR27 | 14 | ---------- ----T----- --- |
| C_BW.96BW0502 | 12 | ---------- ---------- --- |
| C_IN.11246 | 12 | ---------- ---------- --- |
| C_IN.301904 | 12 | ---------- ---------- --- |
| C_IN.301905 | 12 | ---------- ---------- --- |
| C_IN.21068 | 12 | ---------- ---------- --- |
| C_IN.301999 | 12 | ---------- ---------- --- |
| C_BR.92BR025 | 12 | ---------- ---------- --- |
| C_ET.ETH2220 | 12 | ---------- ---------- --- |
| D_ZR.Z2Z6 | 12 | ---------- ---------- --- |
| D_ZR.ELI | 12 | ---------- ---------- --- |
| D_ZR.NDK | 12 | ---------- ---------- --- |
| D_ZR.84ZR085 | 12 | ---------- ---------- --- |
| D_UG.94UG114 | 12 | ---------- ---------- --- |
| F_VI850 | 12 | ---------- ---------- --- |
| F_FI.FIN9363 | 12 | ---------- ---------- --- |
| F_BR.93BR020 | 12 | ---------- ---------- --- |
| G_FI.HH8793-11 | 12 | ---------- ---------- --- |
| G_SE.SE6165 | 12 | ---------- ---------- --- |
| G_BE.DRCBL | 12 | ---------- ---------- --- |
| H_BE.VI991 | 15 | ---------- ---------- -C- |
| H_BE.VI997 | 12 | ---------- ---------- --- |
| H_CF.90CF056 | 12 | ---------- ---------- --- |
| J_SE.SE92809 | 12 | ---------- ---------- --- |
| J_SE.SE91733 | 12 | ---------- ---------- --- |
| AB_RU.KAL153-2 | 12 | ---------- ---------- --- |
| AC_ZM.ZAM184 | 12 | ---------- ---------- --- |
| AC_RW.92RW009 | 12 | ---------- ---------- --- |
| AC_IN.21301 | 16 | ---------- ---------- G-- |
| ADI_ZR.MAL | 12 | ---------- ---------- --- |
| AE_CF.90CF402 | 17 | ---------- A--------- --- |
| AE_TH.CM240 | 12 | ---------- ---------- --- |
| AE_TH.93TH253 | 12 | ---------- ---------- --- |
| AG_NG.IBNG | 12 | ---------- ---------- --- |
| AG_DJ.DJ264 | 12 | ---------- ---------- --- |
| AG_DJ.DJ263 | 12 | ---------- ---------- --- |
| AG_NG.92NG003 | 12 | ---------- ---------- --- |
| AG_NG.92NG083 | 12 | ---------- ---------- --- |
| AGI_ZR.Z321B | 12 | ---------- ---------- --- |

TABLE II-continued

Common primers and probes

| | | |
|---|---|---|
| AGI_CY.94CY0323 | 12 | ---------- ---------- --- |
| AGI_GR.97PVCH | 12 | ---------- ---------- --- |
| AGI_GR.97PVMY | 18 | -------A-- ---------- --- |
| AGJ_AU.BFP90 | 12 | ---------- ---------- --- |
| BF_BR.93BR029 | 12 | ---------- ---------- --- |
| N_CM.YBF30 | 12 | ---------- ---------- --- |
| O_CM.MVP5180 | 12 | ---------- ---------- --- |
| O_CM.ANT70 | 12 | ---------- ---------- --- |
| SIVcpzUS | 14 | ---------- ----T----- --- |
| SIVCPZANT | 27 | ---------- -------AC- T-- |
| SIVCPZGAB | 12 | ---------- ---------- --- |

HIV-common-R (R-out-4929-21)

| | SEQ ID NO | |
|---|---|---|
| QUERY | 19 | CGGGTYTATT ACAGRGACAG C |
| A_SE.SE8131 | 19 | ---------- ---------- - |
| A_SE.UGSE8891 | 19 | ---------- ---------- - |
| A_SE.TZSE8538 | 19 | ---------- ---------- - |
| A_SE.UGSE6594 | 19 | ---------- ---------- - |
| A_KE.Q2317 | 19 | ---------- ---------- - |
| A_SE.UGSE7535 | 19 | ---------- ---------- - |
| A_SE.SOSE7253 | 19 | ---------- ---------- - |
| A_UG.92UG037 | 20 | -------G-- ---------- - |
| A_UG.U455 | 19 | ---------- ---------- - |
| B_US.DH193 | 19 | ---------- ---------- - |
| B_US.896 | 19 | ---------- ---------- - |
| B_US.MN | 19 | ---------- ---------- - |
| B_US.JRCSF | 21 | ---------- ---------A - |
| B_US.JRFL | 19 | ---------- ---------- - |
| B_US.YU10 | 19 | ---------- ---------- - |
| B_US.YU2 | 19 | ---------- ---------- - |
| B_AU.MBC200 | 19 | ---------- ---------- - |
| B_AU.MBC925 | 19 | ---------- ---------- - |
| B_US.BCSG3 | 21 | ---------- ---------A - |
| B_GA.OYI | 19 | ---------- ---------- - |
| B_GB.CAM1 | 19 | ---------- ---------- - |
| B_US.NY5CG | 19 | ---------- ---------- - |
| B_XX.NL43 | 19 | ---------- ---------- - |
| B_FR.LAI | 19 | ---------- ---------- - |
| B_FR.HXB2R | 19 | ---------- ---------- - |
| B_NL.ACH320A | 19 | ---------- ---------- - |
| B_NL.ACH320B | 19 | ---------- ---------- - |
| B_US.SF2CG | 21 | ---------- ---------A - |
| B_US.AD8 | 19 | ---------- ---------- - |
| B_DE.D31 | 19 | ---------- ---------- - |
| B_GB.MANC | 19 | ---------- ---------- - |
| B_DE.HAN2 | 19 | ---------- ---------- - |
| B_US.WEAU160 | 19 | ---------- ---------- - |
| B_US.RF | 19 | ---------- ---------- - |
| B_CN.RL42 | 22 | ---------- ------G--- - |
| B_US.WR27 | 19 | ---------- ---------- - |
| C_BW.96BW0502 | 19 | ---------- ---------- - |
| C_IN.11246 | 19 | ---------- ---------- - |
| C_IN.301904 | 19 | ---------- ---------- - |
| C_IN.301905 | 19 | ---------- ---------- - |
| C_IN.21068 | 19 | ---------- ---------- - |
| C_IN.301999 | 19 | ---------- ---------- - |
| C_BR.92BR025 | 19 | ---------- ---------- - |
| C_ET.ETH2220 | 19 | ---------- ---------- - |
| D_ZR.Z2Z6 | 19 | ---------- ---------- - |
| D_ZR.ELI | 19 | ---------- ---------- - |
| D_ZR.NDK | 19 | ---------- ---------- - |
| D_ZR.84ZR085 | 19 | ---------- ---------- - |
| D_UG.94UG114 | 19 | ---------- ---------- - |
| F_VI850 | 19 | ---------- ---------- - |
| F_FI.FIN9363 | 19 | ---------- ---------- - |
| F_BR.93BR020 | 19 | ---------- ---------- - |
| G_FI.HH8793-11 | 23 | ---------- T--------- - |
| G_SE.SE6165 | 19 | ---------- ---------- - |
| G_BE.DRCBL | 19 | ---------- ---------- - |
| H_BE.VI991 | 19 | ---------- ---------- - |
| H_BE.VI997 | 19 | ---------- ---------- - |
| H_CF.90CF056 | 19 | ---------- ---------- - |
| J_SE.SE92809 | 19 | ---------- ---------- - |
| J_SE.SE91733 | 19 | ---------- ---------- - |
| AB_RU.KAL153-2 | 19 | ---------- ---------- - |
| AC_ZM.ZAM184 | 19 | ---------- ---------- - |
| AC_RW.92RW009 | 19 | ---------- ---------- - |

TABLE II-continued

Common primers and probes

| | | |
|---|---|---|
| AC_IN.21301 | 19 | ---------- ---------- - |
| ADI_ZR.MAL | 21 | ---------- ---------A - |
| AE_CF.90CF402 | 19 | ---------- ---------- - |
| AE_TH.CM240 | 19 | ---------- ---------- - |
| AE_TH.93TH253 | 19 | ---------- ---------- - |
| AG_NG.IBNG | 19 | ---------- ---------- - |
| AG_DJ.DJ264 | 19 | ---------- ---------- - |
| AG_DJ.DJ263 | 19 | ---------- ---------- - |
| AG_NG.92NG003 | 19 | ---------- ---------- - |
| AG_NG.92NG083 | 19 | ---------- ---------- - |
| AGI_ZR.Z321B | 19 | ---------- ---------- - |

TABLE II-continued

Common primers and probes

| | | |
|---|---|---|
| AGI_CY.94CY0323 | 19 | ---------- ---------- - |
| AGI_GR.97PVCH | 19 | ---------- ---------- - |
| AGI_GR.97PVMY | 19 | ---------- ---------- - |
| AGJ_AU.BFP90 | 19 | ---------- ---------- - |
| BF_BR.93BR029 | 19 | ---------- ---------- - |
| N_CM.YBF30 | 19 | ---------- ---------- - |
| O_CM.MVP5180 | 24 | ---------- -------T-- - |
| O_CM.ANT70 | 19 | ---------- ---------- - |
| SIVcpzUS | 19 | ---------- ---------- - |
| SIVCPZANT | 25 | ------C--- -------T-- - |
| SIVCPZGAB | 19 | ---------- ---------- - |

TABLE 3

HXB2 genome information.

```
LOCUS       HIVHXB2CG   9719 bp ss-RNA   linear   VRL 19-AUG-1999
DEFINITION  Human immunodeficiency virus type 1 (HXB2), complete genome;
            HIV1/HTLV-III/LAV reference genome.
ACCESSION   K03455 M38432
VERSION     K03455.1 GI:1906382
KEYWORDS    TAR protein; acquired immune deficiency syndrome; complete
            genome; env protein; gag protein; long terminal repeat
            (LTR); pol protein; polyprotein; proviral gene; reverse
            transcriptase; transactivator.
SOURCE      Human immunodeficiency virus type 1.
ORGANISM    Human immunodeficiency virus type 1
            Viruses; Retroid viruses; Retroviridae; Lentivirus; Primate
            lentivirus group.
BASE COUNT  3411 a 1772 c 2373 g 2163 t
ORIGIN
                                                        (SEQ ID NO: 26)
  1 tggaagggct aattcactcc caacgaagac aagatatcct tgatctgtgg atctaccaca
 61 cacaaggcta cttccctgat tagcagaact acacaccagg gccagggatc agatatccac
121 tgacctttgg atggtgctac aagctagtac cagttgagcc agagaagtta gaagaagcca
181 acaaaggaga gaacaccagc ttgttacacc ctgtgagcct gcatggaatg gatgacccgg
241 agagagaagt gttagagtgg aggtttgaca gccgcctagc atttcatcac atggcccgag
301 agctgcatcc ggagtacttc aagaactgct gacatcgagc ttgctacaag gactttccg
361 ctgggacttt ccaggggagg cgtggcctgg gcgggactgg ggagtggcga gccctcagat
421 cctgcatata agcagctgct ttttgcctgt actgggtctc tctggttaga ccagatctga
481 gcctgggagc tctctggcta actagggaac ccactgctta agcctcaata agcttgcct
541 tgagtgcttc aagtagtgtg tgcccgtctg ttgtgtgact ctggtaacta gagatccctc
601 agaccctttt agtcagtgtg gaaaatctct agcagtggcg cccgaacagg gacctgaaag
661 cgaaagggaa accagaggag ctctctcgac gcaggactcg gcttgctgaa gcgcgcacgg
721 caagaggcga ggggcggcga ctggtgagta cgccaaaaat tttgactagc ggaggctaga
781 aggagagaga tgggtgcgag agcgtcagta ttaagcgggg gagaattaga tcgatgggaa
```

TABLE 3-continued

| HXB2 genome information. |
|---|

```
 841 aaaattcggt taaggccagg gggaaagaaa aaatataaat taaaacatat agtatgggca
 901 agcagggagc tagaacgatt cgcagttaat cctggcctgt tagaaacatc agaaggctgt
 961 agacaaatac tgggacagct acaaccatcc cttcagacag gatcagaaga acttagatca
1021 ttatataata cagtagcaac cctctattgt gtgcatcaaa ggatagagat aaaagacacc
1081 aaggaagctt tagacaagat agaggaagag caaaacaaaa gtaagaaaaa agcacagcaa
1141 gcagcagctg acacaggaca cagcaatcag gtcagccaaa attaccctat agtgcagaac
1201 atccaggggc aaatggtaca tcaggccata tcacctagaa ctttaaatgc atgggtaaaa
1261 gtagtagaag agaaggcttt cagcccagaa gtgataccca tgttttcagc attatcagaa
1321 ggagccaccc cacaagattt aaacaccatg ctaaacacag tggggggaca tcaagcagcc
1381 atgcaaatgt taaaagagac catcaatgag gaagctgcag aatgggatag agtgcatcca
1441 gtgcatgcag ggcctattgc accaggccag atgagagaac caaggggaag tgacatagca
1501 ggaactacta gtacccttca ggaacaaata ggatggatga caaataatcc acctatccca
1561 gtaggagaaa tttataaaag atggataatc ctgggattaa ataaaatagt aagaatgtat
1621 agccctacca gcattctgga cataagacaa ggaccaaagg aaccctttag agactatgta
1681 gaccggttct ataaaactct aagagccgag caagcttcac aggaggtaaa aaattggatg
1741 acagaaacct tgttggtcca aaatgcgaac ccagattgta agactatttt aaaagcattg
1801 ggaccagcgg ctacactaga agaaatgatg acagcatgtc agggagtagg aggacccggc
1861 cataaggcaa gagttttggc tgaagcaatg agccaagtaa caaattcagc taccataatg
1921 atgcagagag gcaattttag gaaccaaaga aagattgtta agtgtttcaa ttgtggcaaa
1981 gaagggcaca cagccagaaa ttgcagggcc cctaggaaaa agggctgttg gaaatgtgga
2041 aaggaaggac accaaatgaa agattgtact gagagacagg ctaatttttt agggaagatc
2101 tggccttcct acaagggaag gccagggaat tttcttcaga gcagaccaga gccaacagcc
2161 ccaccagaag agagcttcag gtctggggta gagacaacaa ctccccctca gaagcaggag
2221 ccgatagaca aggaactgta tcctttaact tccctcaggt cactctttgg caacgacccc
2281 tcgtcacaat aaagataggg gggcaactaa aggaagctct attagataca ggagcagatg
2341 atacagtatt agaagaaatg agtttgccag gaagatggaa accaaaaatg atagggggaa
2401 ttggaggttt tatcaaagta agacagtatg atcagatact catagaaatc tgtggacata
2461 aagctatagg tacagtatta gtaggaccta cacctgtcaa cataattgga agaaatctgt
2521 tgactcagat tggttgcact ttaaattttc ccattagccc tattgagact gtaccagtaa
2581 aattaaagcc aggaatggat ggcccaaaag ttaaacaatg gccattgaca gaagaaaaaa
2641 taaaagcatt agtagaaatt tgtacagaga tggaaaagga agggaaaatt tcaaaaattg
2701 ggcctgaaaa tccatacaat actccagtat ttgccataaa gaaaaagac agtactaaat
2761 ggagaaaatt agtagatttc agagaactta ataagagaac tcaagacttc tgggaagttc
2821 aattaggaat accacatccc gcagggttaa aaagaaaaa atcagtaaca gtactggatg
2881 tgggtgatgc atattttca gttcccttag atgaagactt caggaagtat actgcattta
2941 ccatacctag tataaacaat gagacaccag ggattagata tcagtacaat gtgcttccac
3001 agggatggaa aggatcacca gcaatattcc aaagtagcat gacaaaaatc ttagagcctt
3061 ttagaaaaca aaatccagac atagttatct atcaatacat ggatgatttg tatgtaggat
3121 ctgacttaga aatagggcag catagaacaa aaatagagga gctgagacaa catctgttga
```

TABLE 3-continued

HXB2 genome information.

```
3181 ggtggggact taccacacca gacaaaaaac atcagaaaga acctccattc ctttggatgg
3241 gttatgaact ccatcctgat aaatggacag tacagcctat agtgctgcca gaaaaagaca
3301 gctggactgt caatgacata cagaagttag tggggaaatt gaattgggca agtcagattt
3361 acccagggat taaagtaagg caattatgta aactccttag aggaaccaaa gcactaacag
3421 aagtaatacc actaacagaa gaagcagagc tagaactggc agaaaacaga gagattctaa
3481 aagaaccagt acatggagtg tattatgacc catcaaaaga cttaatagca gaaatacaga
3541 agcaggggca aggccaatgg acatatcaaa tttatcaaga gccatttaaa aatctgaaaa
3601 caggaaaata tgcaagaatg aggggtgccc acactaatga tgtaaaacaa ttaacagagg
3661 cagtgcaaaa aataaccaca gaaagcatag taatatgggg aaagactcct aaatttaaac
3721 tgcccataca aaaggaaaca tgggaaacat ggtggacaga gtattggcaa gccacctgga
3781 ttcctgagtg ggagtttgtt aatacccctc ccttagtgaa attatggtac cagttagaga
3841 aagaacccat agtaggagca gaaaccttct atgtagatgg ggcagctaac agggagacta
3901 aattaggaaa agcaggatat gttactaata gaggaagaca aaaagttgtc accctaactg
3961 acacaacaaa tcagaagact gagttacaag caatttatct agctttgcag gattcgggat
4021 tagaagtaaa catagtaaca gactcacaat atgcattagg aatcattcaa gcacaaccag
4081 atcaaagtga atcagagtta gtcaatcaaa taatagagca gttaataaaa aaggaaaagg
4141 tctatctggc atgggtacca gcacacaaag gaattggagg aaatgaacaa gtagataaat
4201 tagtcagtgc tggaatcagg aaagtactat ttttagatgg aatagataag gcccaagatg
4261 aacatgagaa atatcacagt aattggagag caatggctag tgattttaac ctgccacctg
4321 tagtagcaaa agaaatagta gccagctgtg ataaatgtca gctaaaagga gaagccatgc
4381 atggacaagt agactgtagt ccaggaatat ggcaactaga ttgtacacat ttagaaggaa
4441 aagttatcct ggtagcagtt catgtagcca gtggatatat agaagcagaa gttattccag
4501 cagaaacagg gcaggaaaca gcatattttc ttttaaaatt agcaggaaga tggccagtaa
4561 aaacaataca tactgacaat ggcagcaatt tcaccggtgc tacggttagg gccgcctgtt
4621 ggtgggcggg aatcaagcag gaatttggaa ttccctacaa tccccaaagt caaggagtag
4681 tagaatctat gaataaagaa ttaagaaaaa ttataggaca ggtaagagat caggctgaac
4741 atcttaagac agcagtacaa atggcagtat tcatccacaa ttttaaaaga aaggggggga
4801 ttggggggta cagtgcaggg gaaagaatag tagacataat agcaacagac atacaaacta
4861 aagaattaca aaaacaaatt acaaaaattc aaaattttcg ggtttattac agggacagca
4921 gaaatccact ttggaaagga ccagcaaagc tcctctggaa aggtgaaggg gcagtagtaa
4981 tacaagataa tagtgacata aaagtagtgc caagaagaaa agcaaagatc attagggatt
5041 atggaaaaca gatggcaggt gatgattgtg tggcaagtag acaggatgag gattagaaca
5101 tggaaaagtt tagtaaaaca ccatatgtat gtttcaggga agctagggga tggttttat
5161 agacatcact atgaaagccc tcatccaaga ataagttcag aagtacacat cccactaggg
5221 gatgctagat tggtaataac aacatattgg ggtctgcata caggagaaag agactggcat
5281 ttgggtcagg gagtctccat agaatggagg aaaaagagat atagcacaca agtagaccct
5341 gaactagcag accaactaat tcatctgtat tactttgact gtttttcaga ctctgctata
5401 agaaaggcct tattaggaca catagttagc cctaggtgtg aatatcaagc aggacataac
5461 aaggtaggat ctctacaata cttggcacta gcagcattaa taacaccaaa aaagataaag
```

TABLE 3-continued

HXB2 genome information.

```
5521 ccacctttgc ctagtgttac gaaactgaca gaggatagat ggaacaagcc ccagaagacc
5581 aagggccaca gagggagcca cacaatgaat ggacactaga gcttttagag gagcttaaga
5641 atgaagctgt tagacatttt cctaggattt ggctccatgg cttagggcaa catatctatg
5701 aaacttatgg ggatacttgg gcaggagtgg aagccataat aagaattctg caacaactgc
5761 tgtttatcca ttttcagaat tgggtgtcga catagcagaa taggcgttac tcgacagagg
5821 agagcaagaa atggagccag tagatcctag actagagccc tggaagcatc caggaagtca
5881 gcctaaaact gcttgtacca attgctattg taaaaagtgt tgctttcatt gccaagtttg
5941 tttcataaca aaagccttag gcatctccta tggcaggaag aagcggagac agcgacgaag
6001 agctcatcag aacagtcaga ctcatcaagc ttctctatca aagcagtaag tagtacatgt
6061 aacgcaacct ataccaatag tagcaatagt agcattagta gtagcaataa taatagcaat
6121 agttgtgtgg tccatagtaa tcatagaata taggaaaata ttaagacaaa gaaaaataga
6181 caggttaatt gatagactaa tagaaagagc agaagacagt ggcaatgaga gtgaaggaga
6241 aatatcagca cttgtggaga tgggggtgga tgggggcac catgctcctt gggatgttga
6301 tgatctgtag tgctacagaa aaattgtggg tcacagtcta ttatggggta cctgtgtgga
6361 aggaagcaac caccactcta ttttgtgcat cagatgctaa agcatatgat acagaggtac
6421 ataatgtttg ggccacacat gcctgtgtac ccacagaccc caacccacaa gaagtagtat
6481 tggtaaatgt gacagaaaat tttaacatgt ggaaaaatga catggtagaa cagatgcatg
6541 aggatataat cagtttatgg gatcaaagcc taaagccatg tgtaaaatta accccactct
6601 gtgttagttt aaagtgcact gatttgaaga atgatactaa taccaatagt agtagcggga
6661 gaatgataat ggagaaagga gagataaaaa actgctcttt caatatcagc acaagcataa
6721 gaggtaaggt gcagaaagaa tatgcatttt tttataaact tgatataata ccaatagata
6781 atgatactac cagctataag ttgacaagtt gtaacacctc agtcattaca caggcctgtc
6841 caaaggtatc ctttgagcca attcccatac attattgtgc cccggctggt tttgcgattc
6901 taaaatgtaa taataagacg ttcaatggaa caggaccatg tacaaatgtc agcacagtac
6961 aatgtacaca tggaattagg ccagtagtat caactcaact gctgttaaat ggcagtctag
7021 cagaagaaga ggtagtaatt agatctgtca atttcacgga caatgctaaa accataatag
7081 tacagctgaa cacatctgta gaaattaatt gtacaagacc caacaacaat acaagaaaaa
7141 gaatccgtat ccagagagga ccagggagag catttgttac aataggaaaa ataggaaata
7201 tgagacaagc acattgtaac attagtagag caaaatggaa taacacttta aaacagatag
7261 ctagcaaatt aagagaacaa tttggaaata ataaaacaat aatctttaag caatcctcag
7321 gaggggaccc agaaattgta acgcacagtt ttaattgtgg aggggaattt ttctactgta
7381 attcaacaca actgtttaat agtacttggt ttaatagtac ttggagtact gaagggtcaa
7441 ataacactga aggaagtgac acaatcaccc tcccatgcag aataaaacaa attataaaca
7501 tgtggcagaa agtaggaaaa gcaatgtatg cccctcccat cagtggacaa attagatgtt
7561 catcaaatat tacagggctg ctattaacaa gagatggtgg taatagcaac aatgagtccg
7621 agatcttcag acctggagga ggagatatga gggacaattg gagaagtgaa ttatataaat
7681 ataaagtagt aaaaattgaa ccattaggag tagcacccac caaggcaaag agaagagtgg
7741 tgcagagaga aaaaagagca gtgggaatag gagctttgtt ccttgggttc ttgggagcag
7801 caggaagcac tatgggcgca gcctcaatga cgctgacggt acaggccaga caattattgt
```

TABLE 3-continued

| HXB2 genome information. |

```
7861 ctggtatagt gcagcagcag aacaatttgc tgagggctat tgaggcgcaa cagcatctgt
7921 tgcaactcac agtctggggc atcaagcagc tccaggcaag aatcctggct gtggaaagat
7981 acctaaagga tcaacagctc ctggggattt ggggttgctc tggaaaactc atttgcacca
8041 ctgctgtgcc ttggaatgct agttggagta ataaatctct ggaacagatt tggaatcaca
8101 cgacctggat ggagtgggac agagaaatta acaattacac aagcttaata cactccttaa
8161 ttgaagaatc gcaaaaccag caagaaaaga atgaacaaga attattggaa ttagataaat
8221 gggcaagttt gtggaattgg tttaacataa caaattggct gtggtatata aaattattca
8281 taatgatagt aggaggcttg gtaggtttaa gaatagtttt tgctgtactt tctatagtga
8341 atagagttag gcagggatat tcaccattat cgtttcagac ccacctccca accccgaggg
8401 gacccgacag gcccgaagga atagaagaag aaggtggaga gagagacaga gacagatcca
8461 ttcgattagt gaacggatcc ttggcactta tctgggacga tctgcggagc ctgtgcctct
8521 tcagctacca ccgcttgaga gacttactct tgattgtaac gaggattgtg gaacttctgg
8581 gacgcagggg gtgggaagcc ctcaaatatt ggtggaatct cctacagtat tggagtcagg
8641 aactaaagaa tagtgctgtt agcttgctca atgccacagc catagcagta gctgagggga
8701 cagatagggt tatagaagta gtacaaggag cttgtagagc tat~cgccac atacctagaa
8761 gaataagaca gggcttggaa aggattttgc tataagatgg gtggcaagtg gtcaaaaagt
8821 agtgtgattg gatggcctac tgtaagggaa agaatgagac gagctgagcc agcagcagat
8881 agggtgggag cagcatctcg agacctggaa aaacatggag caatcacaag tagcaataca
8941 gcagctacca atgctgcttg tgcctggcta gaagcacaag aggaggagga ggtgggtttt
9001 ccagtcacac ctcaggtacc tttaagacca atgacttaca aggcagctgt agatcttagc
9061 cacttttaa aagaaaaggg gggactggaa gggctaattc actcccaaag aagacaagat
9121 atccttgatc tgtggatcta caacacacaa ggctacttcc ctgattagca gaactacaca
9181 ccagggccag gggtcagata tccactgacc tttggatggt gctacaagct agtaccagtt
9241 gagccagata agatagaaga ggccaataaa ggagagaaca ccagcttgtt acaccctgtg
9301 agcctgcatg ggatggatga cccggagaga gaagtgttag agtggaggtt tgacagccgc
9361 ctagcatttc atcacgtggc ccgagagctg catccggagt acttcaagaa ctgctgacat
9421 cgagcttgct acaagggact ttccgctggg gactttccag ggaggcgtgg cctgggcggg
9481 actggggagt ggcgagccct cagatcctgc atataagcag ctgcttttttg cctgtactgg
9541 gtctctctgg ttagaccaga tctgagcctg ggagctctct ggctaactag ggaacccact
9601 gcttaagcct caataaagct tgccttgagt gcttcaagta gtgtgtgccc gtctgttgtg
9661 tgactctggt aactagagat ccctcagacc cttttagtca gtgtggaaaa tctctagca
```

(Underlined sequences were common primers and probe.)

Table 4, below, was extracted from Table 2 by collecting sequences which showed mismatches. By using two degenerate oligonucleotides (Y, R, S) in each primer and probe, the number of templates totaled eighteen. In order to validate whether these primers and probes can amplify all groups and subtypes, eighteen oligonucleotide templates were synthesized, which exhibited mismatches at appropriate locations (Table 4).

TABLE 4

Template oligonucleotides for mismatch analysis

F-in-4794-28

| TEMPLATE NO. | QUERY | SEQ ID 4 | GC AGTATTYATY CACAATTTTA AAAGAA |
|---|---|---|---|
| 1. | A_UG.92UG037 | 5 | -- ---G------ ---------- ------ |
| 2. | B_US.JRCSF | 4 | -- ---------- ---------- ------ |
| 3. | B_AU.MBC200 | 4 | -- ---------- ---------- ------ |
| 4. | B_GB.MANC | 6 | -- ---------- ---------- -G---- |
| 5. | B_CN.RL42 | 4 | -- ---------- ---------- ------ |
| 6. | B_US.WR27 | 4 | -- ---------- ---------- ------ |
| 7. | G_FI.HH8793-11 | 4 | -- ---------- ---------- ------ |
| 8. | H_BE.VI991 | 4 | -- ---------- ---------- ------ |
| 9. | J_SE.SE92809 | 7 | -- ---------A ---------- ------ |
| 10. | AC_IN.21301 | 4 | -- ---------- ---------- ------ |
| 11. | ADI_ZR.MAL | 5 | -- ---G------ ---------- ------ |
| 12. | AE_CF.90CF402 | 4 | -- ---------- ---------- ------ |
| 13. | AGI_GR.97PVMY | 4 | -- ---------- ---------- ------ |
| 14. | N_CM.YBF30 | 8 | -- G--T------ ---------- ------ |
| 15. | O_CM.MVP5180 | 9 | -- ---C---G-- ---------- ------ |
| 16. | O_CM.ANT70 | 10 | -- -------G-- ---------- ------ |
| 17. | SIVCPZANT | 11 | -- ---GCA---- ---------- ------ |
| 18. | SIVCPZGAB | 5 | -- ---G------ ---------- ------ |

P-1-4827-23

| TEMPLATE NO. | QUERY | SEQ ID 12 | GGG ATTGGGGGRT ACASTGCAGG |
|---|---|---|---|
| 1. | A_UG.92UG037 | 12 | --- ---------- ---------- |
| 2. | B_US.JRCSF | 12 | --- ---------- ---------- |
| 3. | B_AU.MBC200 | 13 | --- --------AT -T-------- |
| 4. | B_GB.MANC | 12 | --- ---------- ---------- |
| 5. | B_CN.RL42 | 12 | --- ---------- ---------- |
| 6. | B_US.WR27 | 14 | --- ---------- -T-------- |
| 7. | G_FI.HH8793-11 | 12 | --- ---------- ---------- |
| 8. | H_BE.VI991 | 15 | --- ---------- --------C- |
| 9. | J_SE.SE92809 | 12 | --- ---------- ---------- |
| 10. | AC_IN.213101 | 16 | --- ---------- -------G-- |

TABLE 4-continued

Template oligonucleotides for mismatch analysis

| NO. | | SEQ ID | |
|---|---|---|---|
| 11. | ADI_ZR.MAL | 12 | --- ---------- ---------- |
| 12. | AE_CF.90CF402 | 17 | --- -------A-- ---------- |
| 13. | AGI_GR.97PVMY | 18 | --- ----A----- ---------- |
| 14. | N_CM.YBF30 | 12 | --- ---------- ---------- |
| 15. | O_CM.MVP5180 | 12 | --- ---------- ---------- |
| 16. | O_CM.ANT70 | 12 | --- ---------- ---------- |
| 17. | SIVCPZANT | 27 | --- ---------- ----AC-T-- |
| 18. | SIVCPZGAB | 12 | --- ---------- ---------- |

R-out-4929-21

| TEMPLATE NO. | QUERY | SEQ ID 19 | CGGGTYTATT ACAGRGACAG C |
|---|---|---|---|
| 1. | A_UG.92UG037 | 20 | -------G-- ---------- - |
| 2. | B_US.JRCSF | 21 | ---------- ---------A - |
| 3. | B_AU.MBC200 | 19 | ---------- ---------- - |
| 4. | B_GB.MANC | 19 | ---------- ---------- - |
| 5. | B_CN.RL42 | 22 | ---------- ------G--- - |
| 6. | B_US.WR27 | 19 | ---------- ---------- - |
| 7. | G_FI.HH8793-11 | 23 | ---------- T--------- - |
| 8. | H_BE.VI991 | 19 | ---------- ---------- - |
| 9. | J_SE.SE92809 | 19 | ---------- ---------- - |
| 10. | AC_IN.213101 | 19 | ---------- ---------- - |
| 11. | ADI_ZR.MAL | 21 | ---------- ---------A - |
| 12. | AE_CF.90CF402 | 19 | ---------- ---------- - |
| 13. | AGI_GR.97PVMY | 19 | ---------- ---------- - |
| 14. | N_CM.YBF30 | 19 | ---------- ---------- - |
| 15. | O_CM.MVP5180 | 24 | ---------- -------T-- - |
| 16. | O_CM.ANT70 | 19 | ---------- ---------- - |
| 17. | SIVCPZANT | 25 | ------C--- -------T-- - |
| 18. | SIVCPZGAB | 19 | ---------- ---------- - |

As shown in FIGS. 1-2, all templates except for numbers three and seventeen demonstrated similar amplification curves at the concentration of 10 fM under the PCR conditions of forty-five cycles of 95° C. for 30 seconds, 50° C. annealing for 1 minute, followed by 60° C. extension for 1 minute. Templates three and seventeen were also amplified, although these two templates showed shallow slopes (FIG. 1) and higher Ct values (FIG. 2). As shown in FIG. 3, these primer-probe systems worked well for HIV patients.

Moreover, as described above, although the data presented resulted from TaqMan PCR, these oligonucleotide sequences can be used for the other real time PCR technologies described above, including systems using intercalating dyes such as SYBR Green, systems in which a probe hybridizes to the amplicons to generate a fluorescent signal, such as molecular beacons, dual-hybe probes, Sunrise or Amplifluor, and Scorpion, as well as the Policeman system. Moreover, these oligonucleotides can be also used for other gene amplification technologies (NASBA and bDNA).

While the invention has been described in detail and with reference to specific embodiments, it will be apparent to one skilled in the art that various changes and modifications may be made to such embodiments without departing from the spirit and scope of the invention.

What is claimed is:

1. A set of isolated oligonucleotides comprising,
   (a) a first plurality of each of the four different oligonucelotides having the sequence of SEQ ID NO: 4 or the fully complementary sequences thereto,
   (b) a second plurality of each of the four different oligonucleotides having the sequence of SEQ ID NO: 12 or the fully complementary sequences thereto, and
   (c) a third plurality of each of the four different oligonucleotides having the sequence of SEQ ID NO: 19, or the fully complementary sequences thereto.

2. A method for detecting the presence of HIV, said method comprising:
   (a) providing a nucleic acid sample;
   (b) amplifying a target nucleic acid sequence of HIV within said nucleic acid sample using a first plurality of each of the four different oligonucelotides having the sequence of SEQ ID NO: 4 or the fully complementary sequences thereto and a second plurality of each of the four different oligonucleotides having the sequence of SEQ ID NO: 19 or the fully complementary sequences thereto as primers; and
   (c) detecting the presence of the amplification products of the target sequence of HIV as an indication of the presence of HIV.

3. The method of claim 2, said detecting step comprising hybridizing, to the target nucleic acid sequence, at least one of the plurality of each of the four different oligonucleotides having the sequence of SEQ ID NO: 12 or the fully complementary sequence thereto.

4. The method of claim 2, further comprising providing a PCR reaction mixture comprising:
   said nucleic acid sample;
   a set of oligonucleotide primers comprising a plurality of each of the eight different oligonucleotides from the first and second plurality of different primers having the sequence of SEQ ID NO:4 and SEQ ID NO:19, or the fully complementary sequences thereto;
   a nucleic acid polymerase having 5' to 3' nuclease activity;
   a nucleic acid binding compound; and
   a set of each of the four oligonucleotide probes having the sequence of SEQ ID NO:12 or the fully complementary sequence thereto, capable of hybridizing to a region of said target nucleic acid sequence;

wherein said oligonucleotide probe hybridizes within said target nucleic acid sequence bounded by said oligonucleotide primers, said oligonucleotide probe is covalently labeled with a light-emitting label, said nucleic acid binding compound is capable of modifying the light emission of said label, and the light emission of said label in said reaction mixture is measured.

5. The method of claim 2, further comprising providing a PCR reaction mixture comprising:
   said nucleic acid sample;
   a set of oligonucleotide primers comprising a plurality of each of the eight different oligonucleotides from the first and second plurality of different primers having the sequence of SEQ ID NO:4 and SEQ ID NO:19, or the fully complementary sequences thereto;
   a nucleic acid polymerase having 5' to 3' nuclease activity; and
   a set of each of the four oligonucleotide probes having the sequence of SEQ ID NO:12 or the fully complementary sequence thereto, capable of hybridizing to a region of said target nucleic acid sequence;
   wherein the PCR reaction mixture is treated under conditions for PCR, and the 5' to 3' nuclease activity of the nucleic acid polymerase cleaves probes hybridized to the target nucleic acid sequence.

6. The method of claim 2, further comprising providing a PCR reaction mixture comprising:
   said nucleic acid sample;
   a set of oligonucleotide primers comprising a plurality of each of the eight different oligonucleotides from the first and second plurality of different primers having the sequence of SEQ ID NO:4 and SEQ ID NO:19, or the fully complementary sequences thereto;
   a nucleic acid polymerase; and
   a label that emits light when bound to double-stranded DNA;
   wherein the PCR reaction mixture is treated under conditions for PCR, and the light emission of said label in said reaction mixture is measured.

7. The method of claim 2, further comprising providing a PCR reaction mixture comprising:
   said nucleic acid sample;
   a set of oligonucleotide primers comprising a plurality of each of the eight different oligonucletides from SEQ ID NO: 4 and SEQ ID NO:19, or the fully complementary sequences thereto; and
   a nucleic acid polymerase having 3' to 5' nuclease activity;
   wherein the PCR reaction mixture is treated under conditions for PCR, and the 3' to 5' nuclease activity of the nucleic acid polymerase cleaves a nucleotide at the 3' end of at least one of said oligonucleotide primers.

8. A method for detecting an HIV nucleic acid sequence in a sample using a polymerase chain reaction (PCR), wherein the process comprises:
   (a) providing a PCR reaction mixture comprising: said nucleic acid sample; a plurality of oligonucleotide primers comprising a plurality of each of the eight different oligonucleotides from SEQ ID NO:4 and SEQ ID NO:19, or the fully complementary sequences thereto; a nucleic acid polymerase having 5' to 3' nuclease activity; and a plurality of each of the four different oligonucleotide probes having the sequence of SEQ ID NO:12 or the fully complementary sequence thereto wherein said oligonucleotide probe hybridizes within said HIV nucleic acid sequence bounded by said oligonucleotide primers, and said oligonucleotide probe is covalently labeled with a light-emitting label;
   (b) measuring the light emission of said label in said reaction mixture;
   (c) treating the PCR reaction mixture under conditions for PCR, wherein the 5' to 3' nuclease activity of the nucleic acid polymerase cleaves probes hybridized to the target sequence;
   (d) measuring the light emission of said label in said reaction mixture; and
   (e) determining if said target sequence is present by the difference between the light emission measured in step (b) and the light emission measured in step (d).

9. A kit for amplification of HIV nucleic acid sequences, comprising:
   (a) set of isolated oligonucleotides according to claim 1; and
   (b) reagents for amplification of a target nucleic acid sequence.

10. The kit of claim 9, wherein the reagents comprise:
   a nucleic acid polymerase having 5' to 3' nuclease activity.

* * * * *